United States Patent [19]

Nakagawa et al.

[11] Patent Number: 5,517,027

[45] Date of Patent: May 14, 1996

[54] METHOD FOR DETECTING AND EXAMINING SLIGHTLY IRREGULAR SURFACE STATES, SCANNING PROBE MICROSCOPE THEREFOR, AND METHOD FOR FABRICATING A SEMICONDUCTOR DEVICE OR A LIQUID CRYSTAL DISPLAY DEVICE USING THESE

[75] Inventors: Yoshitsugu Nakagawa; Fusami Soeda, both of Ohtsu; Naohiko Fujino, Amagasaki; Isamu Karino, Amagasaki; Osamu Wada, Amagasaki; Hiroshi Kurokawa, Amagasaki; Koichiro Hori, Itami; Nobuyoshi Hattori, Itami; Masahiro Sekine, Itami; Masashi Ohmori, Itami; Kazuo Kuramoto; Junji Kobayashi, both of Amagasaki, all of Japan

[73] Assignee: Mitsubishi Denki Kabushiki Kaisha, Tokyo, Japan

[21] Appl. No.: 254,771

[22] Filed: Jun. 6, 1994

[30] Foreign Application Priority Data

Jun. 8, 1993 [JP] Japan ................... 5-137190
Dec. 24, 1993 [JP] Japan ................... 5-327774

[51] Int. Cl.$^6$ ................................ H01J 37/00
[52] U.S. Cl. ................. 250/306; 250/307; 356/237
[58] Field of Search ................. 250/306, 307; 356/237

[56] References Cited

U.S. PATENT DOCUMENTS

| | | | |
|---|---|---|---|
| 4,595,289 | 6/1986 | Feldman et al. | 356/237 |
| 4,601,577 | 7/1986 | Gotou et al. | 356/237 |
| 4,871,257 | 10/1989 | Suzuki et al. | 356/237 |
| 5,046,847 | 9/1991 | Nakata et al. | 356/237 |
| 5,117,110 | 5/1992 | Yasutake . | |
| 5,177,559 | 1/1993 | Batchelder et al. . | |
| 5,247,186 | 9/1993 | Toda | 250/307 |
| 5,267,017 | 11/1993 | Uritsky et al. | 356/237 |
| 5,311,275 | 5/1994 | Taniguchi et al. | 356/237 |
| 5,379,347 | 1/1995 | Kato et al. | 356/237 |

FOREIGN PATENT DOCUMENTS

| | | |
|---|---|---|
| 0442630 | 8/1991 | European Pat. Off. . |
| 0527448 | 2/1993 | European Pat. Off. . |
| WO85/03353 | 1/1985 | WIPO . |

OTHER PUBLICATIONS

A. Abraitis et al., "Direct Readout Particle Detection System", *IBM Technical Disclosure Bulletin*, vol. 23, No. 11, Apr. 1981, pp. 4970–4971.

H. M. Marchman et al., "Optically Guided Large–Nanostructure Probe", *Review of Scientific Instruments*, vol. 64, No. 5, May 1993, New York, pp. 1248–1252.

"Analyzing and Estimating Technique for Processing High Performance Semiconductor", *Ultra Clean Tech.*, Series No. 13, published by Realize Co., Ltd., 1992, pp. 110–129.

*Primary Examiner*—Bruce C. Anderson
*Attorney, Agent, or Firm*—Burns, Doane, Swecker & Mathis

[57] ABSTRACT

Method for detecting and examining a slightly irregular surface state is provided which includes the steps of: illuminating a surface of a sample with light beam for detecting the slightly irregular surface state; observing a variation of the light beam occurring due to the slightly irregular surface state to specify the location of the slightly irregular surface state in an x-y plane of the sample; making the location of a probe needle of a scanning probe microscope and the location of the slightly irregular surface state on the sample coincide with each other; and measuring a three-dimensional image of the slightly irregular surface state by means of the scanning probe microscope. The scanning probe microscope for use in the aforementioned method and a method for fabricating a semiconductor device or a liquid crystal display device which utilizes the aforementioned method are also provided.

37 Claims, 13 Drawing Sheets

F I G. 10(a)
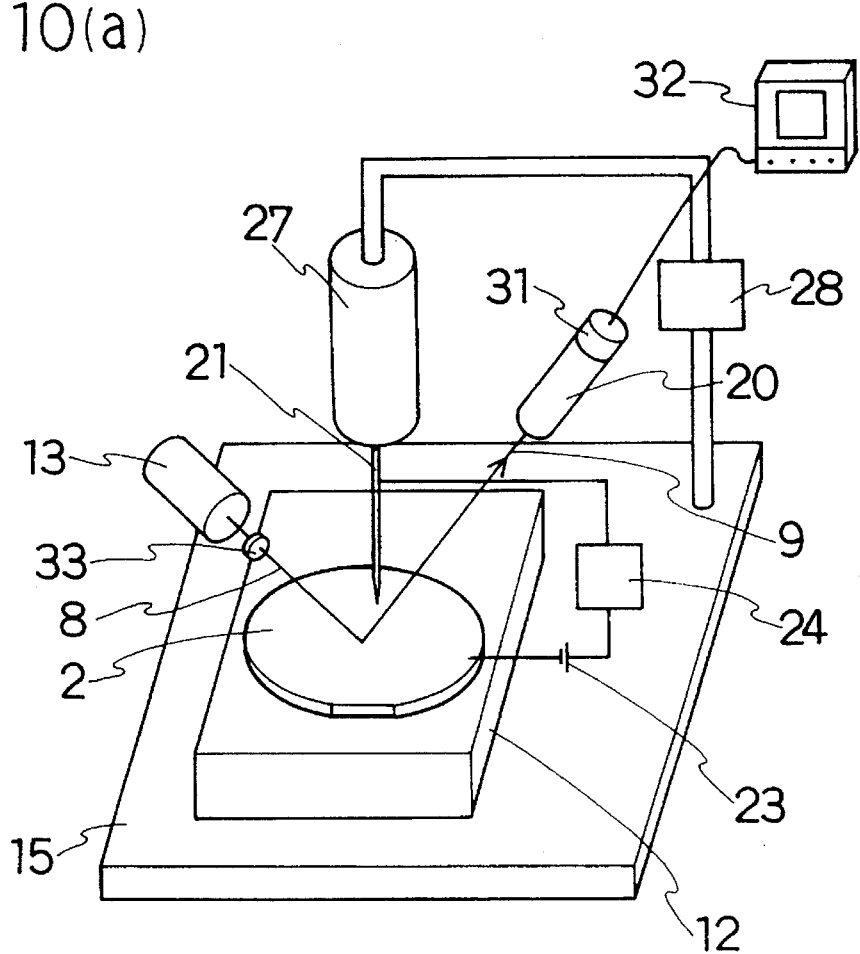
F I G. 10(b)
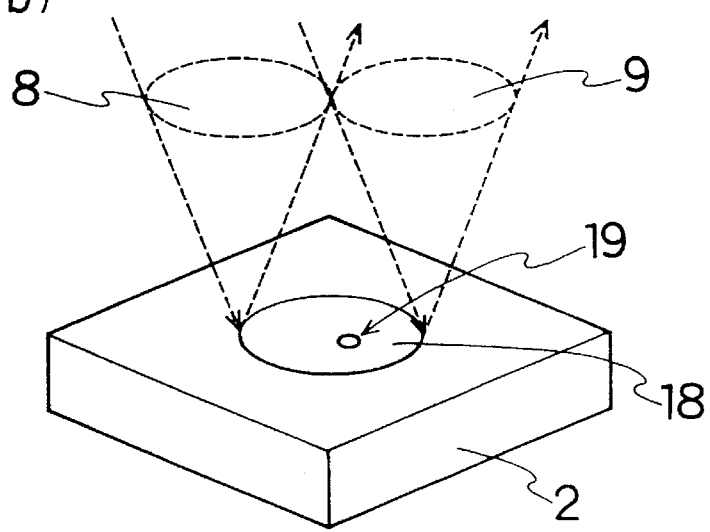

METHOD FOR DETECTING AND EXAMINING SLIGHTLY IRREGULAR SURFACE STATES, SCANNING PROBE MICROSCOPE THEREFOR, AND METHOD FOR FABRICATING A SEMICONDUCTOR DEVICE OR A LIQUID CRYSTAL DISPLAY DEVICE USING THESE

BACKGROUND OF THE INVENTION

The present invention relates to a method for detecting a slightly irregular surface state present on a flat surface of a sample such as a silicon wafer or a glass substrate to be used in a liquid crystal display device. More particularly, it relates to a method for detecting and examining a slightly irregular surface state which enables facilitated observation, analysis, examination and evaluation on a slightly irregular surface state, such as on the three dimensional shape of each slightly irregular surface state, by detecting and locating the slightly irregular surface state using a particle detector having its own coordinate system and linking the coordinates of the slightly irregular surface state to the coordinate system of another analyzer such as a scanning probe microscope thereby specifying the location of the slightly irregular surface state in terms of the coordinate system of the analyzer. The present invention also relates to a scanning probe microscope imparted with functions for the method and to a method for fabricating a semiconductor device or a liquid crystal display device using the foregoing method and microscope.

In the present invention, the words "slightly irregular surface state" includes, for example, a state where fine particles are adhered on a surface, a condition where fine or micro projections and fine or micro pits are present, an abnormal condition caused by a crystal defect or the like. Further, the term "analyzer such as a scanning probe microscope" is meant to include an observing apparatus, an analyzing apparatus, an examining apparatus and an evaluating apparatus, each having an atomic force microscope (AFM), a scanning tunnel microscope (STM), a magnetic force microscope (MFM) or the like.

In the manufacture of VLSIs, typically a 4 Mbit- or 16 Mbit-DRAM, the production yield is known to almost depend upon failures attributable to slightly irregular surface states, such as fine particles adhering to a wafer. This is because with increasingly miniaturizing pattern width slightly irregular surface states which have not been considered critical come to play the role of contaminants. In general, the size of a slightly irregular surface state herein in question is considered as small as the minimum interconnection line width of a VLSI be manufactured reduced by a factor of several units. From this, in the manufacture of a 16 Mbit-DRAM of which the minimun interconnection line width is 0.5 μm, a slightly irregular surface state of the order of 0.1 μm diameter is of concern. Such a slightly irregular surface state acts as a contaminant and hence is responsible for breaks, shortcircuiting of a circuit pattern or the like. This leads to products prone to failure, hence, products of degraded reliability and quality. For that reason, in improving the production yield it is a critical point that the realities of slightly irregular surface states, for example in what conditions they adhere to a sample, be determined and controlled by quantitative measurement and analysis with high precision.

As the means to accomplishing this end, a particle detector has been conventionally used which is capable of detecting a slightly irregular surface state present on a surface of a flat sample such as a silicon wafer. Examples of such conventional particle detectors include IS-2000 and LS-6000, products of Hitachi Electronics Engineering Co., Ltd., SURFSCAN 6200, a product of Tencor Co., USA, and WIS-9000, a product of Estek Co., USA. The measuring principle underlying these particle detectors and the system configuration for realizing these detectors are described in detail in, for exmaple, "Technology for analyzing and evaluating high performance semiconductor processes" edited by Semiconductor substrate technology studies, published by REALIZE Co., Ltd., pp. 111–129.

Figure 11:
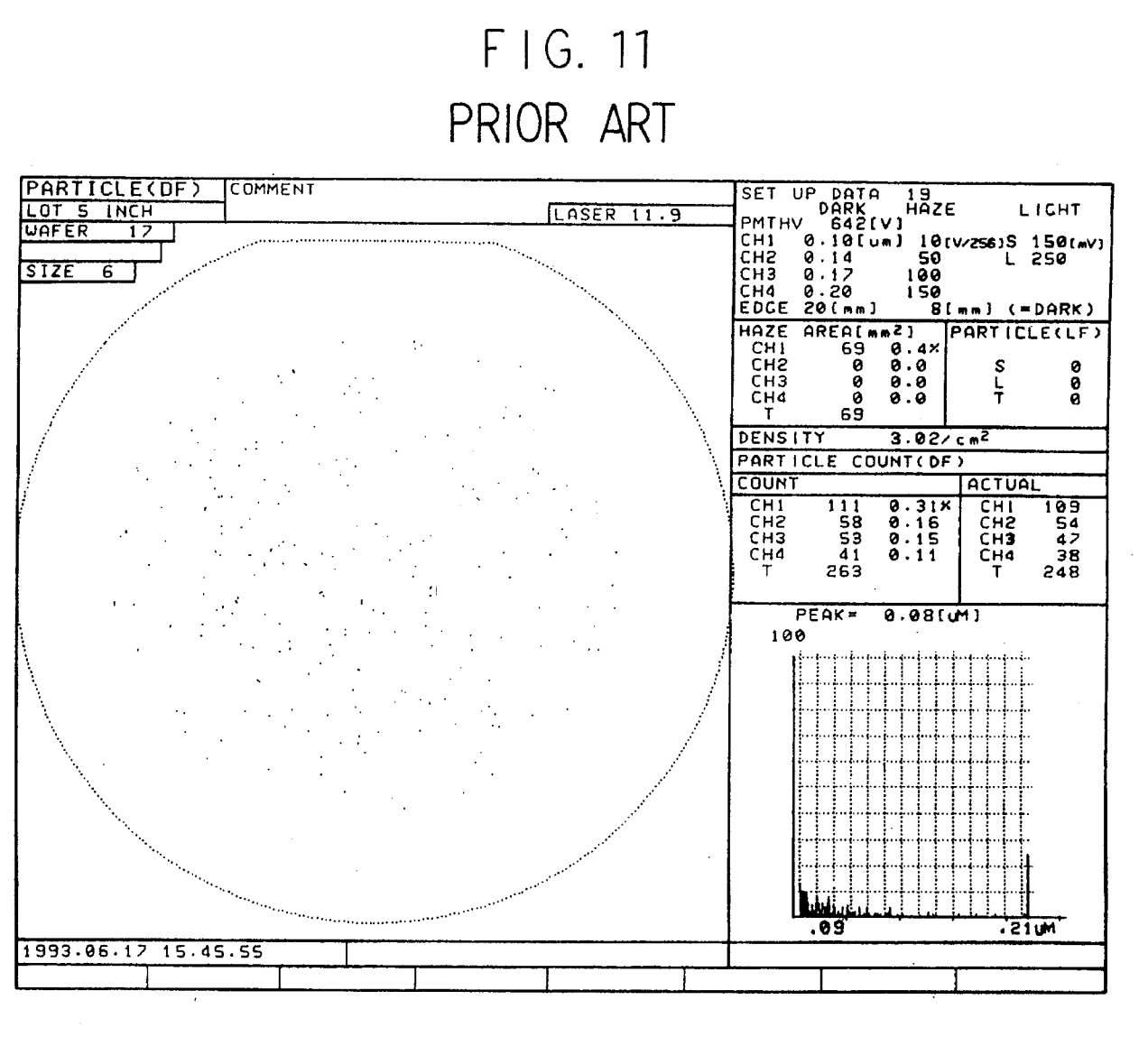

FIG. 11 shows the results of a measurement on slightly irregular surface states (each larger than 0.1 μm in size) present on an existing 6 in. silicon wafer. In FIG. 11 the circle represents the contour of the wafer and the points in the circle correspond to the locations of the slightly irregular surface states.

As seen from FIG. 11, however, the conventional particle detector merely provides such information as the locations and distribution of particle sizes of slightly irregular surface states present on a surface of the sample such as a silicon wafer and cannot identify the realities of the slightly irregular surface states, for example, what forms each slightly irregular surface state.

Also, there has been conventionally used a scanning probe microscope having a high resolution power, such as an atomic force microscope or a scanning tunnel microscope, to observe the three-dimensional microscopic shapes of slightly irregular surface states on a surface of a flat sample such as a silicon wafer.

The atomic force microscope is a device to observe the three-dimensional shape of a surface of a sample by bringing near the surface of the sample a projecting pyramid probe needle such as of $Si_3N_4$ mounted on the tip of a cantilever, scanning the sample in the x-y plane while adjusting the level z of the sample so as to keep the Van Del Waals force exerted between the sample and the probe needle constant (typically about $10^{-9}N$), and monitoring z-axis control signals fed in the scanning operation.

FIGS. 12(a) and 12(b) illustrate the basic configuration of a conventional atomic force microscope (for example, NanoScope AFM produced by Digital Instrument Co.) for use in observing a surface of a sample such as a silicon wafer. In FIG. 12 a probe needle 1 for scanning a surface of a sample 2 is a pyramid-like projection of $Si_3N_4$ mounted on the tip of a cantilever 3. When the probe needle 1 is brought near the sample 2, the cantilever 3 is bent because of the repulsive force produced by mutual contact of atoms. The degree of bending of the cantilever 3 is proportional to the atomic force exerted between the probe needle 1 and the sample 2. The bending of the cantilever 3 is detected by utilizing the variation in the reflecting direction of bending detection laser beam 4 emitted from a laser light source 5 comprising a light-emitting device such as a semiconductor laser and illuminated onto the reflecting surface of the cantilever 3. This is referred to as "optical lever method". Light reflected by the cantilever 3 is detected by a light-receiving device 6 such as a photodiode. While controlling the level of the sample so as to keep the bending of the cantilever 3 constant, the sample is scanned in x-y plane by operating an xyz stirring actuator 7 to measure the three-dimensional shape of the surface of the sample. Control signals applied to the actuator 7 for the movement along each axis in this scanning operation are input to a microcomputer, graphically processed and displayed as the results of the three-dimensional measurement on the sample surface.

The scanning tunnel microscope (STM) is a device for observing the three-dimensional shape of a surface of a sample by bringing a metallic probe needle very near (about 1 nm) the sample, scanning the sample in x-y plane with the metallic needle while controlling the level z of the sample so as to keep the tunnel current flowing between the sample and the needle constant, and monitoring control signals applied for the movement of the sample along z axis in this scanning operation.

FIG. 13 illustrates the basic configuration of a conventional scanning tunnel microscope (for example, NanoScope STM produced by Digital Instrument Co.) for use in observing a surface of a sample such as a silicon wafer. In FIG. 13 a metallic probe needle 21 for scanning a surface of a sample 2 comprises, for example, tungsten filament and is shaped acute at the tip thereof by electropolishing. A bias voltage is applied across the probe needle 21 and the sample 2 from a DC power source 23.

In the three-dimensional measurement of the sample surface, the metallic probe needle 21 applied with bias voltage is brought near the surface of the sample by means of an xyz stirring actuator 27 so as to allow a tunnel current of a predetermined magnitude to flow between the two, the tunnel current being measured and controlled by an ammeter 24. In turn, while controlling the level z of the metallic probe needle 21 so as to keep the magnitude of the tunnel current constant, the probe needle 21 is made to scan the sample in x-y plane by means of the xyz stirring actuator 27. Control signals applied to the actuator 27 for the movement along each axis in this scanning operation are input to a microcomputer, graphically processed and displayed as the results of the three-dimensional measurement on the sample surface.

Incidentally, the conventional atomic force microscope and scanning tunnel microscope are described in detail in, for example, "THE TRC NEWS", vol. 38 (January 1992), pp. 33 to 39, published by Toray Research Center Co., Ltd., and "STM book for easy reading" published by Hitachi Ltd., 1991.

Now, there is a desire to identify slightly irregular surface states in actual conditions by directly observing an individual slightly irregular surface state or analyzing the same to determine the composition thereof with the use of an appropriate analyzer such as a scanning probe microscope. With regard to the conventional analyzers, however, the scanning probe microscope for instance is adapted to bring its probe needle into contact with a surface of a sample at any location and scan the surface, and hence is designed to observe only the condition of the sample surface where the probe needle is able to scan. Therefore, it is very difficult for the scanning probe microscope to position the probe needle thereof at a location where a slightly irregular surface state is present. Accordingly, the scanning probe microscope is unable to satisfactorily respond to the demand to find out and examine very few slightly irregular surface states of submicron order or smaller, such as crystal defects, which are present on a surface of a sample. For instance, when a wafer size of which is 6 in. is compared to the area of the Sado island (area of which is 857 km$^2$) of Japan, a slightly irregular surface state of 0.3 μm size is equivalent in size to a golf ball. It is very hard to detect such a slightly irregular surface state, specify the location thereof and position the probe needle at such location. This makes it nearly impossible to find out any slightly irregular surface state of submicron order or sub-submicron order such as a crystal defect and observe it three-dimensionally. Further, even if the particle detector is previously used to locate a slightly irregular surface state, the location thereof is defined in terms of the coordinate system of the particle detector and, hence, it is difficult to define the location of the slightly irregular surface state in terms of the coordinate system of the analyzer. Still further, since the location of individual slightly irregular surface states on a wafer is defined by a pixel area (typically of 20 μm×200 μm) which depends upon the size of laser beam focused on the wafer, the location is defined with an inherent error equivalent to the area of the pixel used. Where the sample having been subjected to slightly irregular surface state detection by the particle detector is to be set in an analyzer, such as scanning probe microscope, other than the particle detector, an additional error due to shifting of the coordinates is inevitable because of the setting again. For that reason, to identify the realities of a slightly irregular surface state certain measures are required to be taken to completely link the coordinate system of the particle detector to that of the analyzer such as the scanning probe microscope and eliminate the error attributable to a pixel area, or to register the coordinates of the slightly irregular surface state specified by the particle detector into the coordinate system of the analyzer so as to eliminate the error by an approach such as to newly detect the location of a slightly irregular surface state again specified by the particle detector. Note that the focused beam area is about 20 μm×200 μm, which is described in the foregoing literature "Technology for analyzing and evaluating high performance semiconductor processes".

Various particle detectors and scanning probe microscopes were examined for coordinate systems of their x-y stages. As a result, almost all of them were found to employ x-y coordinate system. The coordinate axes and the origin with respect to a wafer as a sample to be measured are determined by the following methods: (1) to assume the flat axis of the orientation flat of the wafer be the x axis (or y axis), a normal line to the x axis in the wafer plane be the y axis ( or x axis ), the intersecting point of the circumference of the wafer and the y axis be a point (0,y), and the intersecting point of the cricumference and the x axis be a point (x,0); and (2) to assume the flat axis of the orientation flat of the wafer be the x axis (or y axis), a normal line to the x axis in the wafer plane be the y axis, and the center of the wafer determined from the equation of circle using three points obtained on the circumference (except the orientation flat) of the wafer be the origin (0,0).

With the above methods, however, these coordinate axes and the origin or center necessarily deviate from one wafer to another or for each setting because of the difference in the circumferential surface precision or in the precise size between wafers or because of the difference between respective positions of wafers set on the stage or of subtle warpage involved in each wafer. As a result, deviation of the coordinate axes and origin with respect to individual wafer is inevitable between the devices employing these methods (e.g., between the particle detector and the analyzer such as scanning probe microscope). Various devices were examined for the amount of a deviation caused by the abovementioned reasons by the use of several wafers each having a lattice pattern. The examination revealed the fact that even between devices of high precision (particle detector: IS-2000 produced by Hitachi Electronics Engineering Co., Ltd., measure SEM: S-7000 produced by Hitachi Ltd.) the origin or center of x-y coordinates and any point defined in terms of the x-y coordinates deviated about (±100 μm,±100 μm). For that reason, when a slightly irregular surface state present on a wafer at any location which has been detected by the particle detector is to be observed, analyzed and evaluated using the analyzer such as the scanning probe microscope, one must observe the region (200 µm×200 µm=40000 µm²) covering the regional range of (±100µm, ±100 µm) or more from the center, or the location where the slightly irregular surface state is considered to be present by the use of the scanning probe microscope to confirm the location of the slightly irregular surface state, and then observe or analyze the slightly irregular surface state by enlarging the slightly irregular surface state or a like process to serve the purpose. For that reason, it takes considerably time for observing or analyzing the slightly irregular surface state.

Attempt is to be made to appreciate the dimensions of the aforesaid region relative to the slightly irregular surface state. Assuming that the region of 40000 µm² (200 µm×200 µm) is observed using a CCD camera having one million pixels which is considered to have a relatively high resolution power, the detection range (area) covered by one pixel of the CCD camera is calculated to make consideration on the size of a smallest detectable slightly irregular surface state. Under the above conditions the detection range covered by one pixel is found to be 0.04 µm² from the calculation: 40000 µm²÷1000000=0.2 µm×0.2 µm. Since a slightly irregular surface state of the size not larger than one pixel is difficult to identify, the limit in the detection of a slightly irregular surface state is 0.04 µm² (0.2µm×0.2 µm). Stated otherwise, it is difficult to directly detect a slightly irregular surface state having a projected area of not larger than 0.04 µm² (equivalent to about 0.2 µm diameter) by means of the CCD camera having one million pixels and, hence, it seems nearly impossible to specify the location of such a slightly irregular surface state.

From the above, it can be understood that it is difficult to directly observe or evaluate a slightly irregular surface state of not larger than about 0.2 µm diameter detected by the conventional particle detector by linking the coordinates of the slightly irregular surface state specified by the detector to the coordinate system of the analyzer such as the scanning probe microscope to specify the location of the slightly irregular surface state in terms of the coordinate system of the analyzer.

The present invention is attained to overcome the foregoing problems. It is, therefore, an object of the present invention to provide a method for easily finding out the location of a slightly irregular surface state present on a surface of a sample, a method for examining a slightly irregular surface state which is capable of selectively and three-dimensionally observing only a defective portion thus detected of the sample surface, and a scanning probe microscope therefor.

It is another object of the present invention to provide a method and apparatus for observing, analyzing and evaluating a slightly irregular surface state by again detecting the slightly irregular surface state of which location is previously detected in terms of the coordinate system of the particle detector by the use of the coordinate system of an analyzer other than the particle detector and linking or registering the location of the slightly irregular surface state specified by the particle detector to the coordinate system of the analyzer with good precision.

It is yet another object of the present invention to provide method and apparatus for observing, analyzing and evaluating a slightly irregular surface state by newly detecting a slightly irregular surface state which cannot be detected by the particle detector by the use of the coordinate system of an analyzer other than the particle detector and registering the location of the slightly irregular surface state in the coordinate system of the analyzer with good precision.

It is a further object of the present invention to improve the yield of semiconductor devices or liquid crystal display devices production and upgrade the reliability of the semiconductor devices or liquid crystal display devices by examining a slightly irregular surface state present on a wafer or a transparent insulative substrate by means of the aforesaid scanning probe microscope in a fabrication process of a semiconductor device or a liquid crystal display device.

SUMMARY OF THE INVENTION

Thus, the present invention provides a method for detecting a slightly irregular surface state, comprising the steps of: illuminating a surface of a sample with light beam for detecting the slightly irregular surface state; and observing a variation of the light beam occurring due to the slightly irregular surface state to specify the location of the slightly irregular surface state in an x-y plane of the sample.

The light beam is preferably a laser light beam because the laser light beam has a keen directionality and hence enhances the contrast ratio reflecting the variation of the light beam occurring due to the slightly irregular surface state, allows assured observation of the slightly irregular surface state and specifies the location of the slightly irregular surface state with good precision.

The variation of the light beam can be observed by sensing irregularly reflected light of the light beam from the dark field thereof or by sensing a dark portion of the light beam from the bright field section thereof.

Preferably, the variation of the light beam is observed by focusing the microscope on the beam spot of the light beam on the surface of the sample or by a light-receiving element disposed as facing opposite to the beam spot of the light beam. This allows facilitated and assured detection of the slightly irregular surface state.

The present invention also provides a method for examining a slightly irregular surface state, comprising the steps of: illuminating a surface of a sample with light beam for detecting the slightly irregular surface state; observing a variation of the light beam occurring due to the slightly irregular surface state to specify the location of the slightly irregular surface state in an x-y plane of the sample; making a probe needle of a scanning probe microscope and the location of the slightly irregular surface state on the sample coincide with each other; and measuring a three-dimensional image of the slightly irregular surface state by means of the scanning probe microscope.

Preferably, the positioning of the probe needle and the slightly irregular surface state is performed by bringing the probe needle of the scanning probe microscope near the sample; observing the variation of the light beam due to the probe needle to set the location of the probe needle in the x-y plane as coordinates $(x_o, y_o)$; finding coordinates $(x_1, y_1)$ of the location of the slightly irregular surface state on the sample specified in the x-y plane; and moving the probe needle or the sample by a distance $(x_1-x_o, y_1-y_o)$.

Preferably, the sample used in the above method is a semiconductor device or a liquid crystal display device under fabrication, or a semiconductor wafer or a transparent insulative substrate on which the semiconductor device or liquid crystal display device is being fabricated in a production process since it is improved in yield of manufacturing the semiconductor device or the liquid crystal display device.

The present invention yet provides a scanning probe microscope for measuring a three dimensional image of a surface of a sample, comprising: an xyz actuator for three-dimensionally adjusting a probe needle of the scanning probe microscope or the sample to bring the probe needle near the sample; a light source for providing light beam for detecting a slightly irregular surface state present on the surface of the sample; a beam variation sensor, disposed in a dark field section of the light beam, for sensing irregularly reflected light of the light beam caused by the slightly irregular surface state; and an x-y actuator for detecting the location of the slightly irregular surface state.

The beam variation sensor may be disposed in a bright field section so as to detect a dark portion developed by the slightly irregular surface state.

The light source is preferably a laser light source.

The present invention still provides an atomic force microscope for measuring a three-dimensional image of a surface of a sample, comprising: a cantilever; a probe needle mounted on a tip of the cantilever and adapted to be brought near the surface of the sample; a light-emitting element and a light-receiving element which are provided for detecting a bent of the cantilever; an xyz adjusting actuator for three-dimensionally stirring the sample or the cantilever; a light source for providing a light beam for detecting a slightly irregular surface state present on the surface of the sample; and an x-y actuator capable of specifying the location of the surface of the sample.

The present invention yet still provides a scanning tunnel microscope for measuring a three-dimensional image of a surface of a sample, comprising: a metallic probe needle adapted to be brought near the surface of the sample for making tunnel current flow between the sample and the metallic probe needle; an xyz actuator for three-dimensionally adjusting the metallic probe needle or the sample; a light source for providing a light beam for detecting a slightly irregular surface state present on the surface of the sample; and an x-y actuator capable of specifying the location of the surface of the sample and registering the location specified.

The present invention further provides a method for detecting a slightly irregular surface state, comprising the steps of: detecting the location of the slightly irregular surface state present on a surface of a sample by means of a particle detector; transferring the sample onto a coordinate stage of a Scanning probe microscope; approximately linking the location of the slightly irregular surface state specified by the particle detector to a coordinate system of the coordinate stage of the scanning probe microscope; illuminating with a light beam a limited region of the surface of the sample which includes the location of the slightly irregular surface state represented in terms of the coordinate system of the coordinate stage to again specify the location of the slightly irregular surface state; and registering the location of the slightly irregular surface state again specified in terms of the coordinate system of the scanning probe microscope.

Preferably, the limited region covers all the regional ranges of errors which are possible to occur when the positional information of the slightly irregular surface state obtained by the particle detector is transmitted to the scanning probe microscope.

The light beam is preferably a laser light beam because the laser light beam assures increased directionality of light not only when a dark portion of a beam spot is to be detected but also when irregularly reflected light from the beam spot is to be detected, thereby enhancing a contrast ratio between the dark portion of the beam spot and the rest thereof or an intensity of scattered light of irregularly reflected light. This results in facilitated detection of the slightly irregular surface state.

The light beam is preferably s-polarized light obtained by, for example, making a light beam pass through a polarizer because s-polarized light assures further increased directionality of light (scattered light) thereof. This allows stray light to be reduced and hence the contrast ratio be upgraded, resulting in facilitated detection of the slightly irregular surface state.

The second detection of the slightly irregular surface state may be achieved by detecting irregularly reflected light of the light beam from a dark field section of the light beam or by detecting a dark portion developed by irregularly reflected light of the light beam from a bright field section of the light beam. In addition the slightly irregular surface state is observed preferably by focusing a microscope provided in the scanning probe microscope onto the beam spot of the light beam on the surface of the sample.

The provision of a CCD camera in an eyepiece portion of the microscope would permit image information to be input to a CRT and hence allow facilitated observation by the microscope and safely protect the user from the light beam.

If the CCD camera is provided with an image intensifier, the camera would enable detection of subtle irregularly reflected light.

The second detection of the slightly irregular surface state may be achieved using a light-receiving element provided in the scanning probe microscope.

Preferably, the visual field of the microscope or the regional range in the surface of the sample from which the light-receiving element senses reflected light is larger than the regional range of the errors. This allows the scanning probe microscope to detect all the slightly irregular surface states detected by the particle detector.

The scanning probe microscope is preferably an atomic force microscope or a scanning tunnel microscope. Such a microscope allows precise observation on a three-dimensional image of the slightly irregular surface state after specifying the location of thereof.

Preferably, the sample used in the above method is a semiconductor device or a liquid crystal display device under fabrication, or a semiconductor wafer or a transparent insulative substrate on which the semiconductor device or liquid crystal display device is being fabricated in a production process.

The present invention still further provides a method for fabricating a semiconductor device comprising the steps of: cleaning, ion implantation, ion diffusion, CVD, etching, exposure and heat treatment, wherein at least one of the steps includes an inspection step utilizing the aforementioned detection method, examination method or scanning probe microscope.

The present invention still provides a method for fabricating a liquid crystal display device, comprising the steps of: forming a TFT substrate having at least a thin film transistor and a pixel electrode on a transparent insulative substrate; forming a counterpart substrate having an opposing electrode; disposing the TFT substrate and the counterpart substrate in opposing relation with each other with a predetermined gap defined therebetween and bonding these substrates at a marginal portion thereof; and introducing a liquid crystal material into the gap, wherein the step of forming the TFT substrate or the counterpart substrate includes the steps of: cleaning, film formation, exposure, etching and ion implantation, at least one of these steps involving an inspection step utilizing the aforementioned detection method, examination method or scanning probe microscope.

In the present invention the variation of the light beam on the surface of the sample is detected from the dark field or the bright field to detect the location of the slightly irregular surface state. For example, when the sample is moved in the x-y plane while observing the beam spot from the dark field, irregularly reflected light of the light beam is not observed from the dark field when the slightly irregular surface state is absent in the portion illuminated since the light beam is totally regularly reflected. On the other hand, when the slightly irregular surface state is present in that portion, the light beam is irregularly reflected as depending on the size of the slightly irregular surface state and, hence, the irregularly reflected light is observed from the dark field. In this case, even if the size of the slightly irregular surface state is rather smaller than the size of the beam spot, the observation of the slightly irregular surface state is also possible. Accordingly, there is no need to reduce the beam spot to a size as large as that of the slightly irregular surface state. Further, if the beam spot is enlarged, the size of an evaluatable area in the surface of the sample in which it can be detected whether the slightly irregular surface state is present or absent, can be increased. As a result, easy detection is achieved on the location $(x_1,y_1)$ of a slightly irregular surface state of the order of submicrons, sub-submicrons or several nanometers.

Where the light beam reflected from the surface of the sample is detected from the bright field, the absence of the slightly irregular surface state in the illuminated portion causes the light beam to be totally regularly reflected and, hence, a dark portion of the beam spot cannot be observed. On the other hand, the presence of the slightly irregular surface state in the illuminated portion causes the light beam to be irregularly reflected in accordance with the surface configuration of the slightly irregular surface state or the like. For that reason, the optical axis of the irregularly reflected light beam is warped and largely deviated from the optical axis of light regularly reflected from mirror-finished other surfaces of the sample. The portion which irregularly reflects the light beam due to a slightly irregular surface state or the like become the dark portion. This allows easy detection of the location of a slightly irregular surface state of the order of sub-submicrons order, as described above. Note that the location of the dark portion of the beam spot observed from the bright field coincides with the location of the slightly irregular surface state. Accordingly, by detecting the light reflected from the surface of the sample from the bright field the location $(x_1,y_1)$ of the slightly irregular surface state can be detected with ease.

Where the particle detector is used together with the analyzer such as a scanning probe microscope in the present invention, detection of the slightly irregular surface state limited region of the surface of the sample which covers all the regional ranges of errors occurring when the respective coordinate system of the two devices are approximately linked to each other, and the location of the slightly irregular surface state defined as $(x_1,y_1)$ is registered into the coordinate system of the analyzer. Consequently, the location of the slightly irregular surface state can readily be detected with good precision even though the deviation in coordinate system between the particle detector and the analyzer is large. For instance, even if such deviation is as large as several thousand microscopes, the use of an objective lens of about X5 magnification will enable the location of the slightly irregular surface state detected by the particle detector to be found within the visual field of the microscope.

The means for specifying the location of the slightly irregular surface state detects the slightly irregular surface state and specifies the location thereof by observing the variation of the light beam spotted. This allows a slightly irregular surface state which is so fine that the particle detector cannot detect it, to be detected and located using the coordinate system of the analyzer.

Further, in the present invention the sample or the probe needle of the scanning probe microscope is moved so that the probe needle is positioned at the location of the slightly irregular surface state. This realizes easy positioning, and measurement and examination of a three-dimensional image of the slightly irregular surface state. For example, when the probe needle of the scanning probe microscope is brought near the illuminated portion of a surface of the sample, the probe needle is also illuminated with the light beam, an irregularly reflected light or dark portion of the light beam appears on the probe needle. By observing the irregularly reflected light or the dark portion from the dark field or the bright field, the location $(x_0,y_0)$ of the tip of the probe needle can readily be set. Even if the tip of the probe needle is not applied with a light beam, the location of the tip of the probe needle can easily be specified since the geometrical structure of the probe needle is known. Accordingly, the location $(x_0,y_0)$ where the tip of the probe needle can readily be also set.

In turn, the sample or the probe needle is moved to the location $(x_0,y_0)$ so that the location $(x_1,y_1)$ of the slightly irregular surface state is relatively moved a distance $(x_1-x_o, y_1-y_0)$. This makes the location of the slightly irregular surface state coincide with the sample observing position with ease. Accordingly, the probe needle can be brought into direct contact with the slightly irregular surface state and, hence, a three-dimensional image of the slightly irregular surface state can be examined easily.

The foregoing detection of the irregularly reflected light or the dark portion from the dark field or the bright field can easily be assured by disposing the microscope or the light-receiving element in the dark or bright field, or positioning the focus of the microscope as coinciding with the location of the beam spot of the light beam on the surface of the sample or disposing the light-receiving element so as to face opposite to the beam spot.

In the method for fabricating a semiconductor device or a liquid crystal display device according to the present invention, a surface of a semiconductor wafer or a transparent insulative substrate is subjected to sampling inspection or 100% inspection according to the aforesaid method for examining a slightly irregular surface state in each fabrication step or a certain fabrication step. Feeding back the results of the inspection to the corresponding step will contribute to a reduction of defective products and to improvements in the fabrication process, production yield and reliability of each product.

BRIEF DESCRIPTION OF THE DRAWINGS

FIGS. 3(a), 3(b) and 3(c) illustrate the image of a slightly irregular surface state measured by the atomic force microscope according to the present invention, wherein FIG. 3(a) illustrates the image of the slightly irregular surface state in plan, and FIGS. 3(b) and 3(c) are sectional views taken along lines b—b and c—c, respectively, of FIG. 3(a) for showing the depth profile of the slightly irregular surface state;

FIGS. 10(a) and 10(b) illustrate yet another example of the method for examining a slightly irregular surface state with the use of a scanning tunnel microscope according to the present invention;

FIG. 11 illustrates one example of the result of measurement on slightly irregular surface states present on a silicon wafer with the use of a particle detector LS-6000;

DETAILED DESCRIPTION

The present invention will now be described in detail with reference to the drawings.

EXAMPLE 1

Figure 1A:
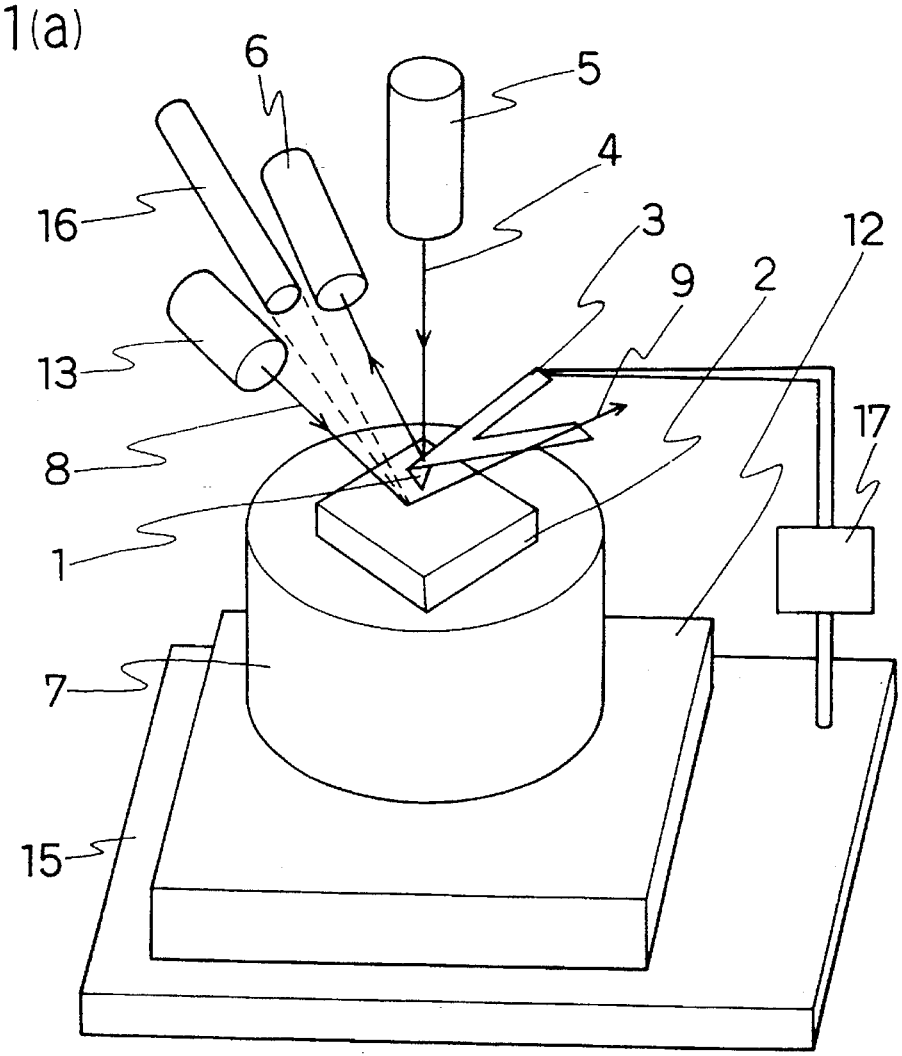
FIGS. 1(a) and 1(b) illustrate the basic configuration of an atomic force microscope for explaining one example of a method for examining a slightly irregular surface state according to the present invention.
Figure 1B:
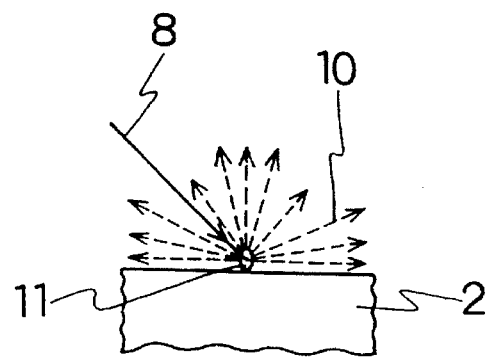
Figure 12A:
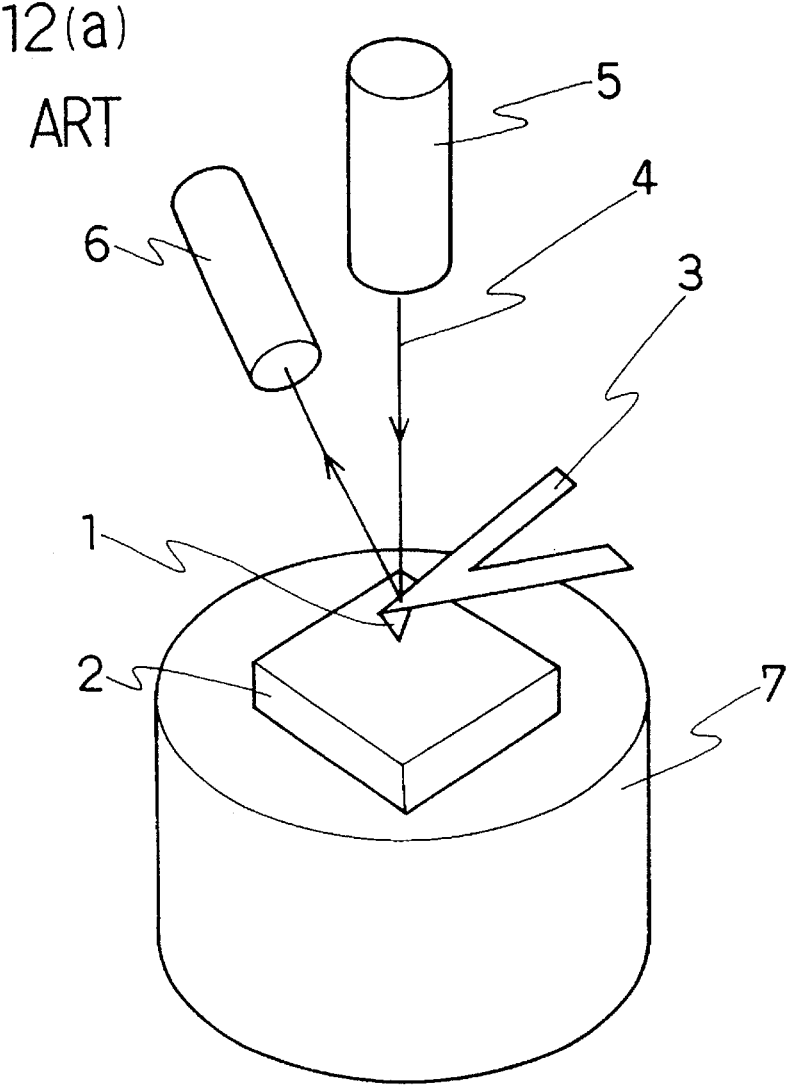
FIGS. 12(a) and 12(b) illustrate the basic configuration of a conventional atomic force microscope.
Figure 12B:
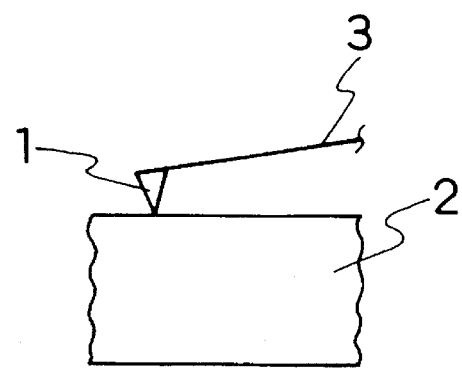
Figure 13:
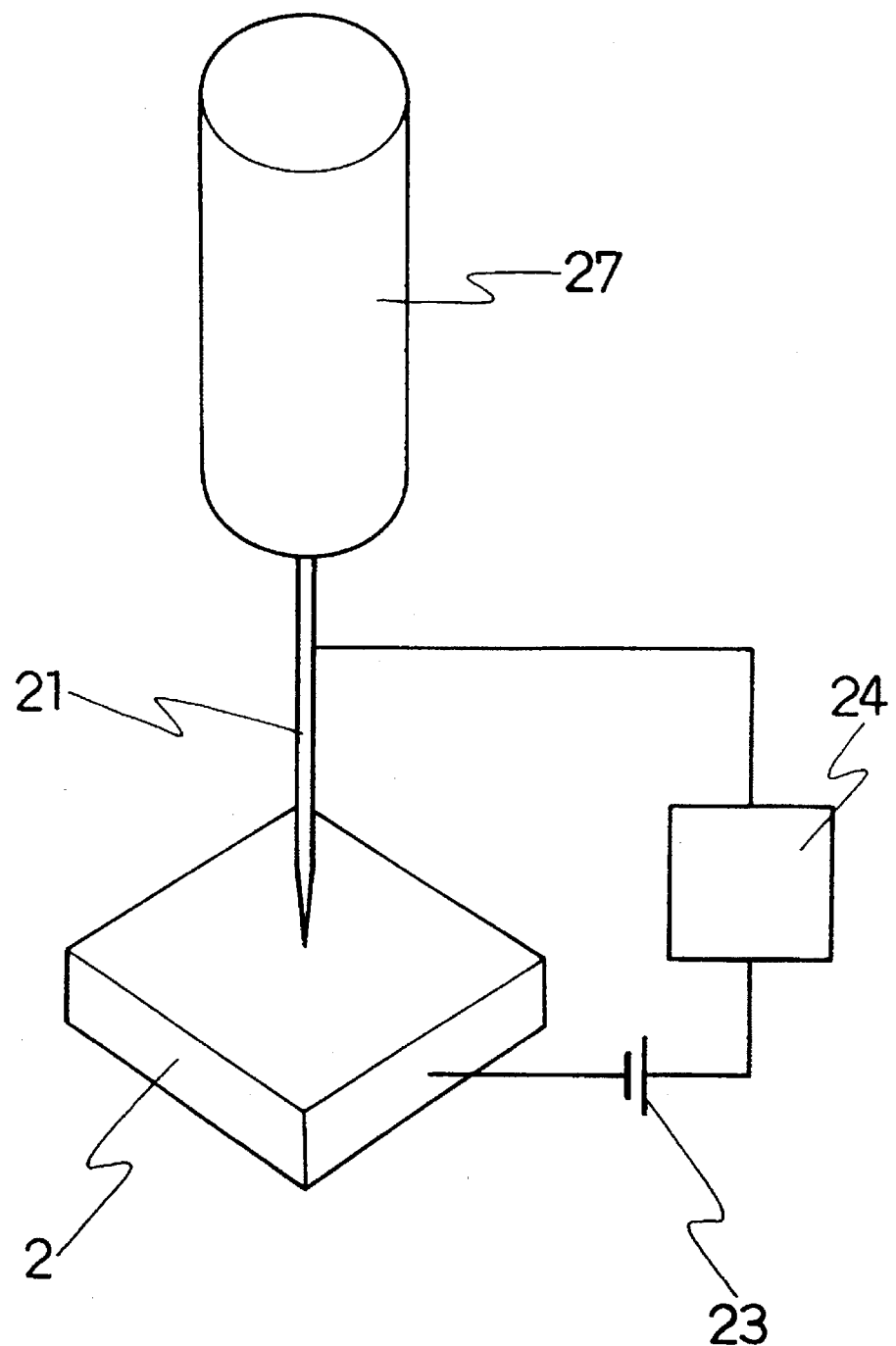
FIG. 13 illustrates the basic configuration of a conventional scanning tunnel microscope.

In FIGS. 1(a) and 1(b), numeral 13 denotes an Ar laser for emitting light beam 8 for detecting a slightly irregular surface state present on a flat sample surface, and numeral 12 denotes an x-y actuator for moving an xyz stirring actuator 7 carrying a sample 2 in an x-y plane. A cantilever 3 is connected to a second x-y actuator 15 adapted to move the cantilever 3 in the x-y plane through an AFM control system 17. Note that same numerals in FIGS. 1 and 12 are used to denote the same or corresponding parts.

Referring to FIG. 1(a) the mirror-polished sample 2 (silicon wafer CZ (plane orientation: 100) produced by MITSUBISHI MATERIALS SILICON CORPORATION which had been previously detected for approximate locations of the slightly irregular surface states using a surface inspection apparatus IS-2000 produced by Hitachi Electronics Engineering Co., Ltd. was illuminated with light beam using the Ar laser 13. In turn, the xyz stirring actuator 7 was driven to lower a probe needle 1 near a surface of the sample 2 while the second x-y actuator 15 was moved in the x-y plane so as to approximately illuminate the light beam 8 onto a region adjacent the tip of the probe needle 1. Then, the positional relation between the Ar laser 13 and the probe needle 1 was adjusted by observing reflected light of the light beam from a dark field section on the Ar laser side by means of a beam variation sensor such as a microscope 16, photodiode or phototransistor. The coordinates indicated by the second x-y actuator at this moment were assumed to be $(x_0, y_0)$. In this case, the focusing point of the microscope 16 was adjusted to coincide with the location on a surface of the sample where the light beam was reflected. Where a light-receiving element such as a photodiode is used instead of the microscope, the light-receiving element is disposed so as to face opposite to the beam-reflecting location.

Figure 2:
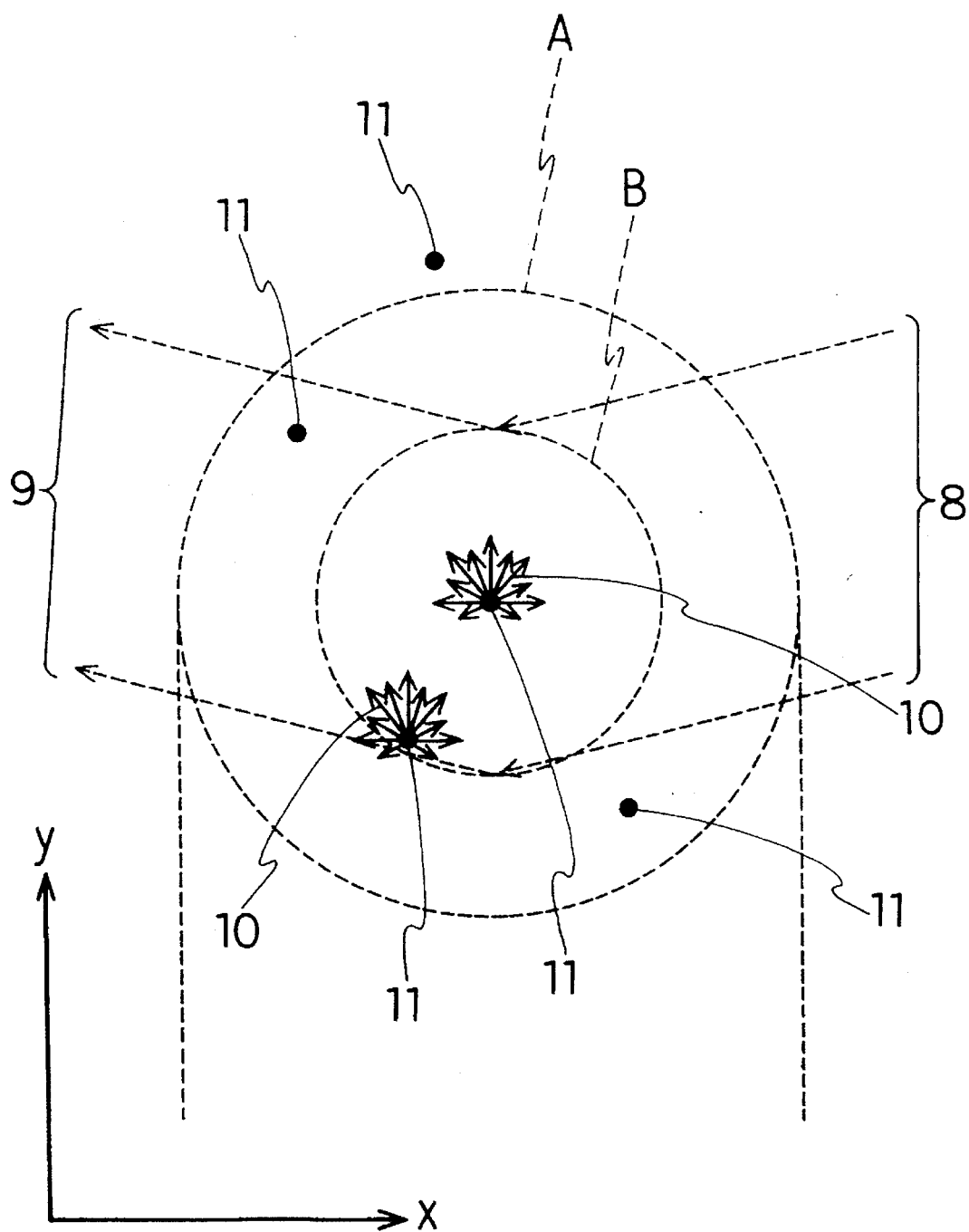
FIG. 2 is a schematic illustration of light beam irregularly reflected due to a slightly irregular surface state when observed from a dark field.

In turn, a surface of the sample 2 was illuminated with the light beam 8 at a location adjacent the location where a slightly irregular surface state was considered to be present, i.e., the aforementioned location previously detected. FIG. 2 is a schematic illustration of light beam 8 spotted on a sample surface, reflected light beam 9, and irregularly reflected light 10 of the light beam caused by the slightly irregular surface state 11 present therein when observed from the dark field section using the microscope 16. In the observation system shown in FIG. 2 the observation visual field range A of the microscope 16 disposed in the dark field section is depicted as covering the beam spot B of the light beam 8 on the sample 2. As shown in FIG. 2, irregularly reflected light 10 appeared at the location of the foreign matter 11 present within the spot B, so that such location was specified by observing the irregularly reflected light 10 by means of the microscope 16. On the other hand, since the light beam 8 was completely regularly reflected at a location where the slightly irregular surface state was absent within the spot, nothing was observed at such location by the microscope 16 disposed in the dark field section. From this, even if the light beam 8 having a spot size B far larger than the slightly irregular surface state is used, the irregularly reflected light 10 caused by the slightly irregular surface state can be observed with the use of the microscope 16 thereby readily specifying the location of the slightly irregular surface state within the beam spot with good precision.

It should be noted that irregular reflection occurs due to a slightly irregular surface state of the size as small as ½ of the wavelength of light beam used, it is possible to exactly specify the location of a slightly irregular surface state of the size as small as or larger than ½ of the wavelength of light beam used. Accordingly, the size of a detectable slightly irregular surface state ranges from submicron order through sub-submicron order to several nanometer order. As a result, even a very small slightly irregular surface state present on a large sample can readily be specified with good precision and efficiently examined within such a range.

In turn, the surface of the sample 2 was observed from the dark field section while operating the x-y actuator 12 in the x-y plane. If a slightly irregular surface state is present in the optical path, irregularly reflected light 10 caused by such a slightly irregular surface state is observed at the coordinates $(x_1, y_1)$ of the x-y actuator 12 (refer to FIGS. 1(b) and 2).

Then, the x-y actuator 12 or the second x-y actuator 15 was moved a distance $(x_1-x_0, y_1-y_0)$ to position the xyz stirring actuator 7 at the position at which the slightly irregular surface state 11 was observed. The xyz stirring actuator 7 was adjusted to bring the probe needle into contact with the target surface of the sample so that atomic force (repulsive force) of about $10^{-9}$ would be exerted therebetween. Irregular reflection of the light beam emitted from, for example, laser light source 5 was then observed using the light-receiving element 6 to achieve measurement by the atomic force microscope.

Figure 3A:
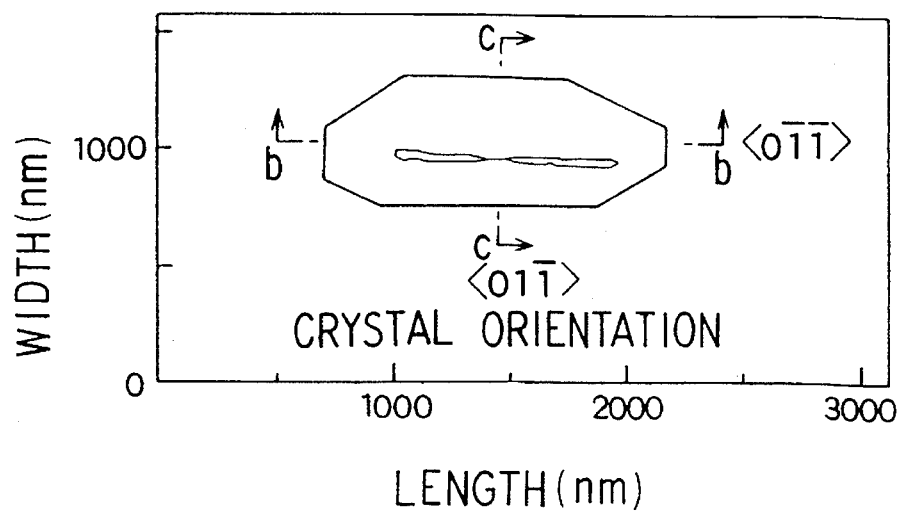
Figure 3B:
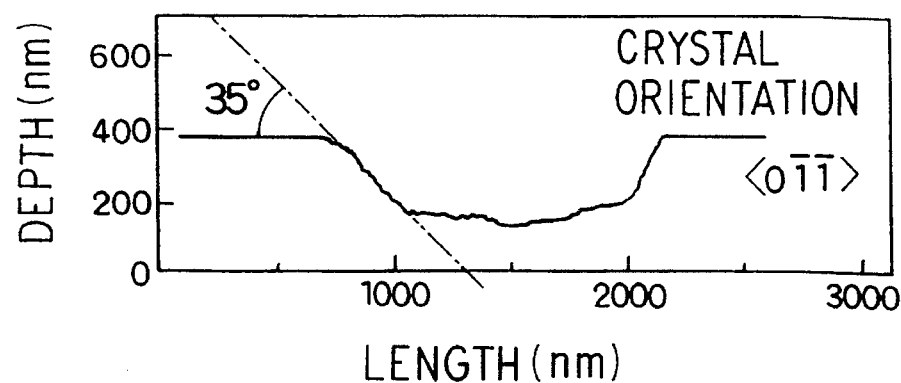
Figure 3C:
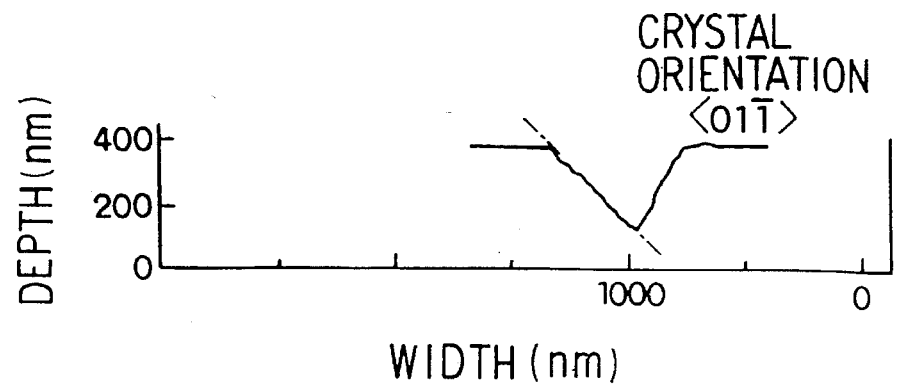

In this way, the three-dimensional shape of the slightly irregular surface state observed at coordinates $(x_1,y_1)$ was measured. FIGS. 3(a), 3(b) and 3(c) show one example of the result of the measurement. FIG. 3(a) illustrates a micro pit of facet present in a surface of a semiconductor wafer, and FIGS. 3(b) and 3(c) are sectional views taken along lines b—b and c—c, respectively, of FIG. 3(a) for showing the profiles of the slightly irregular surface state in depth. It can be understood from FIGS. 3(a) to 3(c) that the slightly irregular surface state 11 is a micro pit of about 1400 nm along b—b line, about 560 nm along c—c line and about 300 nm in maximum depth, which is present on a surface of the silicon wafer.

In this example the light beam source for detecting a slightly irregular surface state comprises the Ar laser because a laser light beam assures a light beam of keen directionality and hence enhances the contrast of the beam spot. Therefore, even a very small slightly irregular surface state can advantageously be located with precision. However, the light source is not limited to the Ar laser but may be another laser light source such as a semiconductor laser or any other light source which emits light beam obtained by reducing infrared ray, white light, visible light, ultraviolet ray or the like into a beam by means of an optical lens or the like. The following examples, too, employ an Ar laser as the light source for detecting a slightly irregular surface state but are not limited thereto. Where photodiodes are used, observation can be achieved by arranging the photodiode like a CCD image sensor.

EXAMPLE 2

Figure 4A:
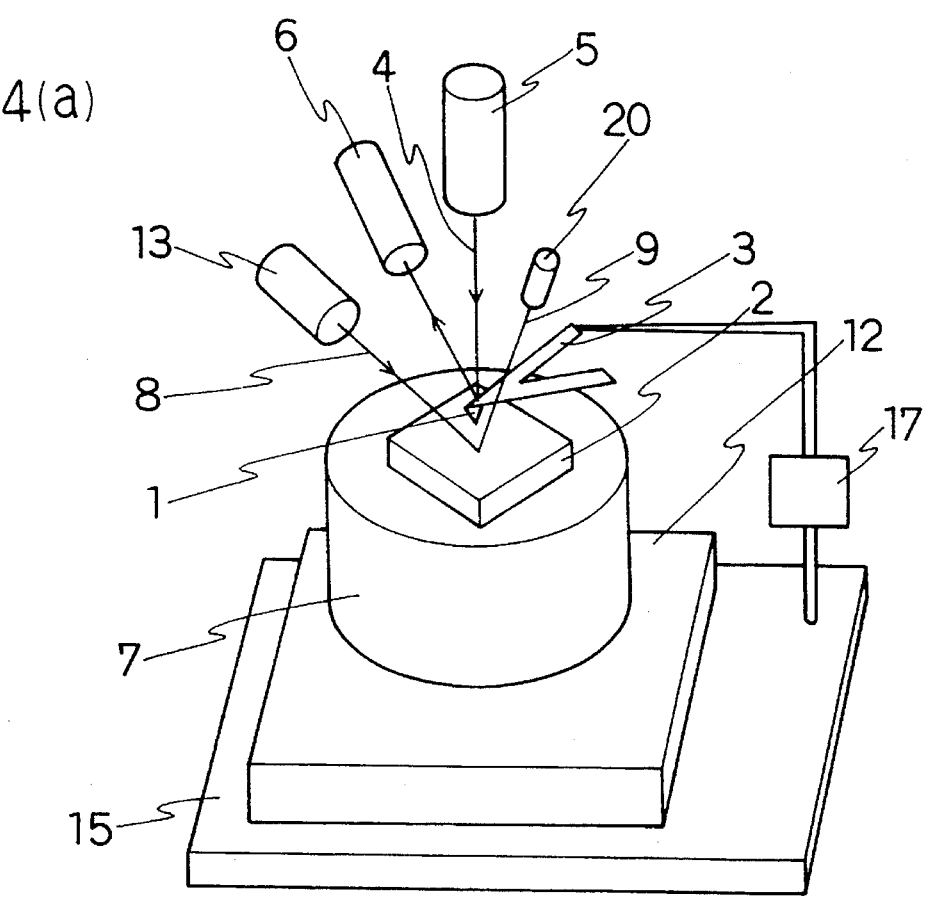
FIGS. 4(a) and 4(b) illustrate another example of the method for examining a slightly irregular surface state with the use of an atomic force microscope according to the present invention.
Figure 4B:
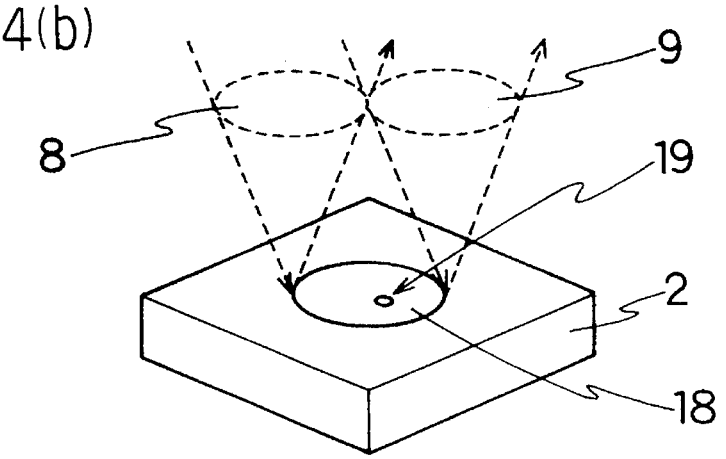

FIGS. 4(a) and 4(b) illustrate another example of the method for detecting a slightly irregular surface state where an atomic force microscope is used as the scanning probe microscope.

In this example the variation of the light beam due to a slightly irregular surface state or due to the tip of the probe needle 1 was observed from the bright field section 9 of the light beam emitted from the Ar laser 13 by means of the microscope 20 to specify the location of the slightly irregular surface state or adjust the positional relation between the slightly irregular surface state and the probe needle. Other features of this example are similar to those of Example 1, and in FIGS. 4(a) and 4(b) like numerals are used to denote like parts of FIGS. 1(a) and 1(b). In addition the positioning of the sample 2 or of the probe needle 1 was conducted under the same conditions as in Example 1.

The method of detecting the variation of light beam from the bright field section of the light beam according to this example was as follows:

When a slightly irregular surface state was absent within a beam spot 18 of the light beam 8 illuminating a surface of the sample 2, the light beam 8 was regularly reflected by the surface of the sample and, hence, the overall spot 18 was observed bright with no dark portion when observed from the bright field section by means of the microscope 20. When the slightly irregular surface state was present within the beam spot 18, the light beam 8 running toward the slightly irregular surface state was prevented from being regularly reflected by the slightly irregular surface state. Accordingly, a dark portion 19 was observed at a location coincident with the location of the slightly irregular surface state when the reflected a light beam was observed (refer to FIG. 4(b)). This allowed the location of the dark portion 19 to be specified as $(x_1,y_1)$. In turn, as in Example 1, the x-y actuator 12 or the second x-y actuator 15 was moved a distance $(x_1-x_0,y_1-y_0)$ to position the slightly irregular surface state as to coincide with the probe needle 1. Thus, the three-dimensional shape of the slightly irregular surface state was measured by means of the atomic force microscope. Although the microscope 20 was used to observe the reflected light 9, there may be used any other means capable of detecting the variation of the light beam, such as a beam variation sensor comprising a light-receiving element, for example a photodiode or a phototransistor, the beam variation sensor being disposed as facing opposite to the beam spot. Where the photodiode are used, arranging it like a CCD image sensor will allow the observation of the dark portion.

EXAMPLE 3

Figure 5A:
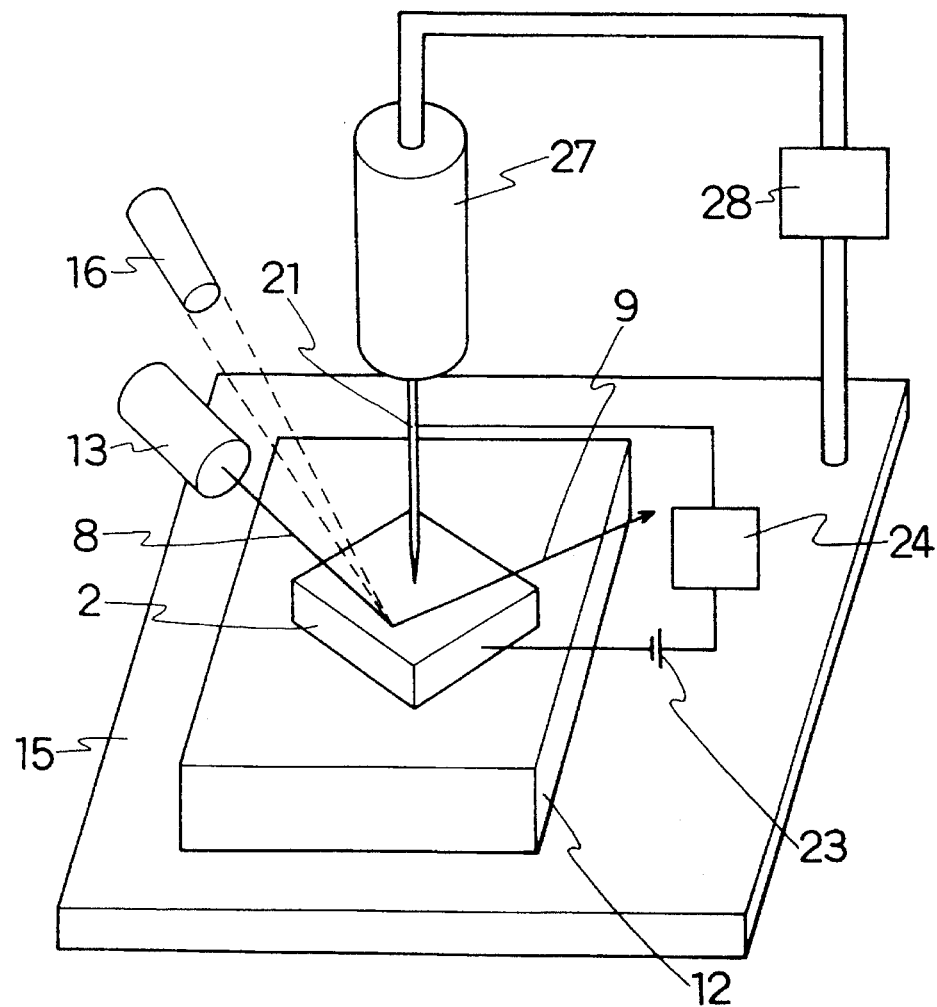
FIGS. 5(a) and 5(b) illustrate the basic configuration of a scanning tunnel microscope for explaining another example of the method for examining a slightly irregular surface state according to the present invention.
Figure 5B:
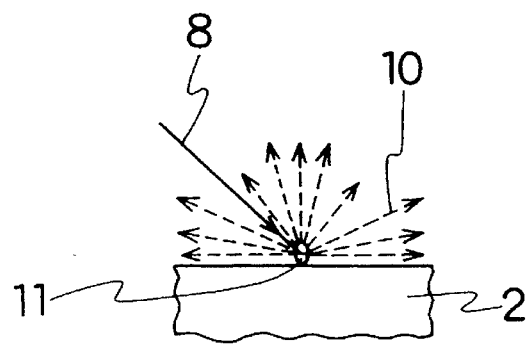

FIGS. 5(a) and 5(b) illustrate the basic configuration of a scanning tunnel microscope as another example of the scanning probe microscope for use in another example of the method for detecting a slightly irregular surface state according to the present invention. In FIGS. 5(a) and 5(b), numeral 13 denotes an Ar laser provided for illuminating the sample with a light beam for detecting a slightly irregular surface state 11 present on a surface of the sample, and numeral 12 denotes an x-y actuator provided for scanning the sample 2 in the x-y plane. A metallic probe needle 21 is connected to a second x-y actuator 15 adapted to move the probe needle 21 in the x-y plane through an STM control system 28. In FIGS. 5(a) and 5(b), like numerals are used to denote the same or corresponding parts of FIGS. 1(a) 1(b), 12(a), 12(b) or 13.

As shown in FIG. 5(a), in substantially the same way as in Example 1 a surface of the sample 2 comprising a mirror-polished silicon wafer (CZ produced by MITSUB-ISHI MATERIALS SILICON CO., plane orientation (100)) was illuminated with the light beam 8 using the Ar laser 13. An xyz stirring actuator 27 was then driven to lower a metallic probe needle 21 near a surface of the sample 2 while the second x-y actuator 15 is moved in the x-y plane so as to approximately illuminate the light beam 8 onto a region adjacent the tip of the probe needle 21. This adjustment was achieved by observing reflected light from the dark field section by means of a beam variation sensor such as the microscope 16 or a photodiode. The coordinates indicated by the second x-y actuator 15 at this moment were $(x_3,y_3)$. In this case, the focusing point of the microscope 15 was adjusted to coincide with the location on a surface of the sample 2 where the light beam 8 was reflected. Where the photodiode is used instead of the microscope, the photodiode is disposed so as to face opposite to the beam-reflecting location.

In turn, a surface of the sample 2 was illuminated with the light beam 8 at a location adjacent the location where a slightly irregular surface state was considered to be present. When the slightly irregular surface state 11 was absent in the optical path, the light beam 8 was regularly reflected by the surface of the sample and, hence, reflected laser light 9 was not observed from the dark field section. In turn, the surface of the sample 2 was observed from the dark field section as in Example 1 while moving the x-y actuator 12 in the x-y plane. When the slightly irregular surface state 11 was present in the optical path, irregularly reflected light 10 was observed at the coordinates $(x_4,y_4)$ defined by the x-y actuator 12 (refer to FIG. 5(b)).

Then, the x-y actuator 12 or the second x-y actuator 15 was moved a distance $(x_4-x_3,y_4-y_3)$ so that the location of the slightly irregular surface state 11 would be shifted to the sample-observing position. Thereafter, the xyz stirring actuator was adjusted to bring the metallic probe needle 21 into contact with the target surface of the sample 2, thereby measuring the slightly irregular surface state 11 using the scanning tunnel microscope.

In this way the three-dimensional measurement on the slightly irregular surface state observed at $(x_4,y_4)$ gave the same result as in Example 1.

EXAMPLE 4

Figure 6A:
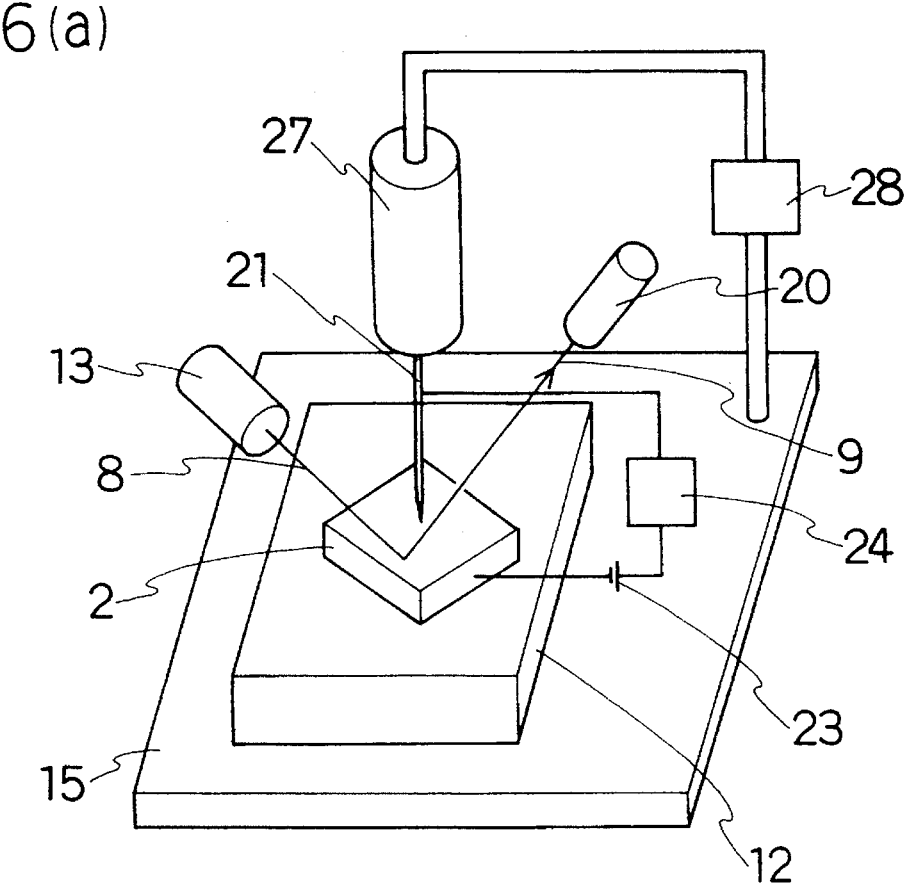
FIGS. 6(a) and 6(b) illustrate yet another example of the method for examining a slightly irregular surface state with the use of a scanning tunnel microscope according to the present invention.
Figure 6B:
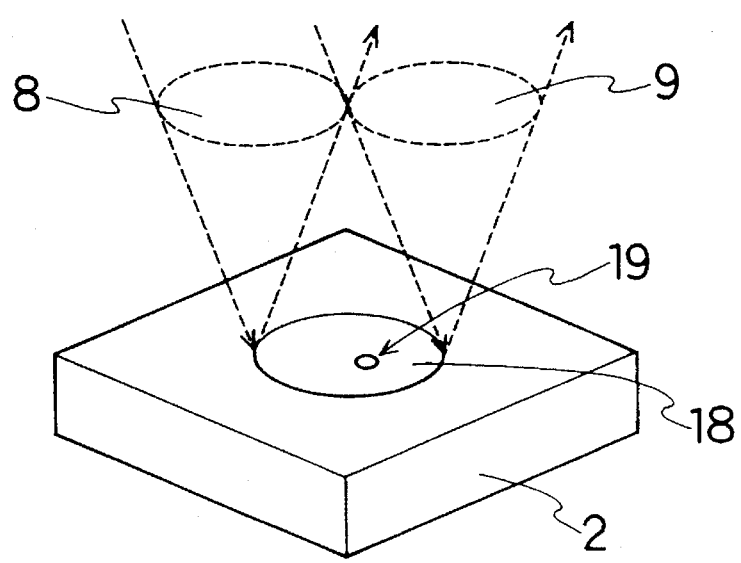

FIGS. 6(a) and 6(b) illustrate another example of the method for detecting a slightly irregular surface state according to the present invention where a scanning tunnel microscope is used as the scanning probe microscope.

In this example, the variation of the light beam due to a slightly irregular surface state or due to the tip of the probe needle 1 was observed from the bright field section of the light beam emitted from the Ar laser 13 by means of the microscope 20 to specify the location of the slightly irregular surface state or adjust the positional relation between the slightly irregular surface state and the probe needle 1. Other features of the example are similar to those of Example 1, and in FIG. 6 like numerals are used to denote the same parts of FIG. 5. In addition, the positioning of the sample 2 or of the probe needle 1 with respect to the sample was conducted under the same conditions as in Example 1.

The method of detecting the variation of light beam from the bright field section of the light beam 8 according to this example was the same as in Example 2. Accordingly, when the slightly irregular surface state was absent within a beam spot 18 of the light beam 8, a dark portion 19 was not observed within the beam spot 18 by a beam variation sensor such as the microscope 20. On the other hand, when the slightly irregular surface state was present within the beam spot 18, a dark portion 19 was observed at a location coincident with the location of the slightly irregular surface state thereby specifying the location $(x_3,y_3)$ of the slightly irregular surface state. In this case, the focusing point of the microscope 20 was made to coincide with the location on a surface of the sample where the light beam 8 was reflected, i.e., the location of the beam spot 18. Where a light-receiving element such as a photodiode is used as the light source, it is disposed as facing opposite to the beam spot 18.

In this manner the probe needle 21 of the scanning tunnel microscope was made to coincide with the slightly irregular surface state and the three-dimensional shape of the slightly irregular surface state was measured as in the foregoing examples.

EXAMPLE 5

Figure 7A:
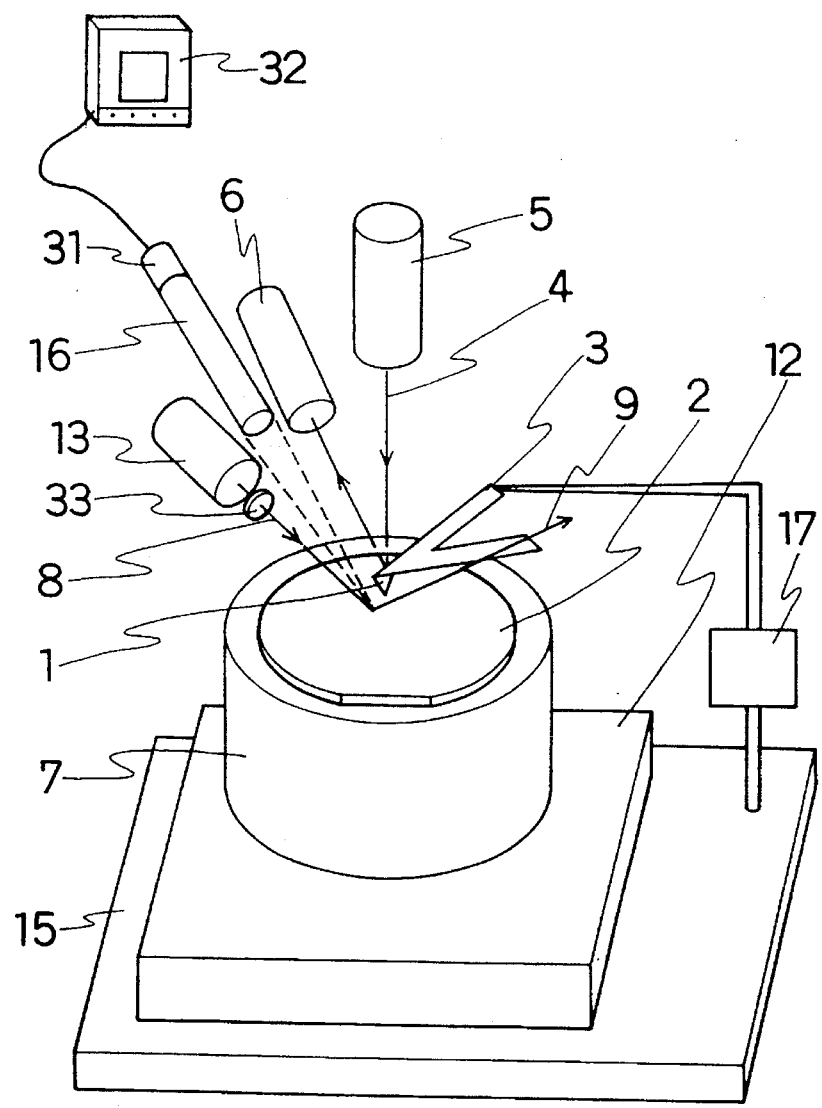
FIGS. 7(a) and 7(b) illustrate the basic configuration of a atomic force microscope for explaining another example of the method for examining a slightly irregular surface state according to the present invention.
Figure 7B:
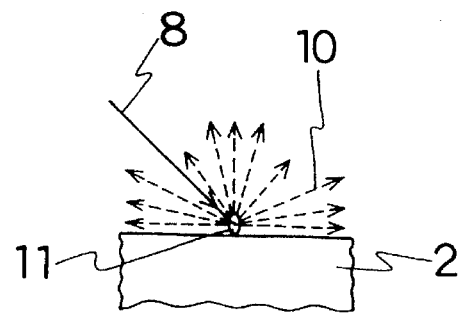

FIGS. 7(a) and 7(b) illustrate the basic configuration of an atomic force microscope as an example of the scanning probe microscope for use in another example of the method for detecting a slightly irregular surface state according to the present invention. Referring to FIGS. 7(a) and 7(b) illustrate the output power of an Ar laser 13 was 15 mW, and a polarizer 33 was adapted to polarize the light beam 8 in various directions. A CCD camera 31 having an image intensifier was mounted on a microscope 16 provided for observing a surface of the sample 2 illuminated by the Ar laser 13 from the dark field section. A CRT 32 is adapted to output the image of the observed surface. This example employed a silicon wafer as the sample 2. An x-y actuator 12 was provided to move an xyz stirring actuator 7 carrying the sample 2 (capable of carrying a silicon wafer of the size up to 8 in. diameter) in the x-y plane. In FIGS. 7(a) and 7(b) illustrate like numerals are used to denote the same or corresponding parts of FIGS. 1(a), 1(b), 12(a) and 12(b).

Initially, a plurality of mirror-polished silicon wafers 2 (6 in. silicon wafers (plane orientation: 100), trade name: CZ, product of MITSUBISHI MATERIALS CO. ) were subjected to a particle detector (SURFSCAN 6200 produced by Tencor Co., USA) to observe the approximate size and location of a slightly irregular surface state present on the silicon wafers. On each silicon wafer were randomly present about 80 slightly irregular surface states of the order of 0.1 to 0.2 µm diameter and about three slightly irregular surface states of the order of 0.2 to 0.3 µm diameter.

In turn, three points on the circumference (except for orientation flat) of each wafer 2 set on the xyz stirring actuator 7 were measured with the flat axis of the orientation flat assumed to be the x axis and with a normal line to the x axis in the plane of the wafer assumed to be the y axis. From the results of the measurement, the center (0,0) of the wafer was calculated using the equation of circle. The mirror-polished surface of the silicon wafer 2 was then illuminated with the light beam 8 using the Ar laser 13. The xyz stirring actuator 7 was then driven to lower the probe needle 1 near a surface of the wafer 2 while the second x-y actuator 15 was moved in the x-y plane, so that the light beam 8 was applied onto a region adjacent the tip of the probe needle 1. The positional relation between the Ar laser 13 and the probe needle 1 was adjusted by observing the reflected light from the dark field of the Ar laser 13 by means of, for example, the CRT 32 connected to the microscope 16 or photodiode, thereby centering the location of the tip of the probe needle 1 in the visual field of the microscope. Note that the location of the tip of the probe needle 1 need not necessarily be centered in the visual field, and it may be placed at a predetermined location in the visual field. The objective lens and eyepiece of the microscope used this time each had X5 magnification, and the microscope was able to cover a visual field of about 2 mm diameter at the largest setting. The coordinates indicated by the second x-y actuator 15 at this moment were $(x_0,y_0)$. The focusing point of the microscope 16 was made to coincide with the location on the silicon wafer where the light beam 8 was reflected. The size of the light beam 8 was about 2 mm×about 4 mm. Where a photodiode is used instead of the microscope, the photodiode is disposed as facing opposite to such location where the light beam 8 is reflected.

In turn, the xyz stirring actuator 7 was driven to make the probe needle 1 go away from the surface of the wafer 2.

The silicon wafer 2 was then moved to a position coincident with the location where the slightly irregular surface state was considered to be present, i.e., the location of which approximate coordinates had been previously detected using the particle detector, by moving the second x-y actuator 15 so as to bring the wafer to the target position where the light beam should be applied.

In turn, the surface of the silicon wafer 2 was observed from the dark field section while moving the x-y actuator 12 in the x-y plane, as in the foregoing examples. When the slightly irregular surface state was present in the optical path, irregularly reflected light 10 was observed at the coordinates ($x_1,y_1$) defined by the x-y actuator 12 (refer to FIG. 7(b)).

In this case, when the slightly irregular surface state 11 was absent in the optical path, the light beam 8 was regularly reflected by the surface of the silicon wafer 2 and, hence, the reflected light 9 was not observed from the dark field section. The results of the observation were as shown in the schematic illustration of FIG. 2 and are explained as in Example 1.

With respect to the silicon wafers 2 thus evaluated, reflected light was assuredly observed at at least one point within a visual field of about 2 mm diameter covered by the microscope, such point being coincident with the approximate coordinates of the location where the slightly irregular surface state 11 was considered to be present on the surface of the silicon wafer 2 which had been previously detected by the particle detector. Note that in almost all the observations reflected light was observed at one point, and the observations of reflected light at plural points were rare. The intensity of the reflected light thus observed grew higher with increasing output of the Ar laser 13. Further, a slightly irregular surface state on the order of 0.2 to 0.3 μm diameter was responsible for reflected light of a higher intensity than reflected light caused by a slightly irregular surface state on the order of 0.1 to 0.2 μm diameter. The intensity of reflected light output by the CRT 32 grew higher as the detection sensitivity of the CCD camera 31 having the image intensifier was enhanced. In addition, the surface of the silicon wafer was made brightest and the S/N ratio was enhanced when the light beam was s-polarized light. Assuming that location nm where reflected light was observed is the location of slightly irregular surface state n, the location nm was centered or placed at a predetermined location in the visual field of the microscope, and the coordinates ($x_n,y_m$) indicated by the x-y actuator 12 at this moment were registered as the location of the slightly irregular surface state n.

Then, the x-y actuator 12 or the second x-y actuator 15 was moved a distance ($x_n-x_0,y_m-y_0$), i.e., the slightly irregular surface state n was moved to a location coincident with the tip of the probe needle 1. The xyz stirring actuator 7 was then adjusted to bring the probe needle 1 into contact with the surface of the silicon wafer so that an atomic force (repulsive force) of about $10^{-9}$ would be exerted therebetween. In this way, the measurement using the atomic force microscope was performed. Thus, the three-dimensional shape of the slightly irregular surface state n observed at ($x_n,y_m$) was measured. There were observed various types of slightly irregular surface states such as adhered fine particles or micro projections and those like scratches.

EXAMPLE 6

Figure 8A:
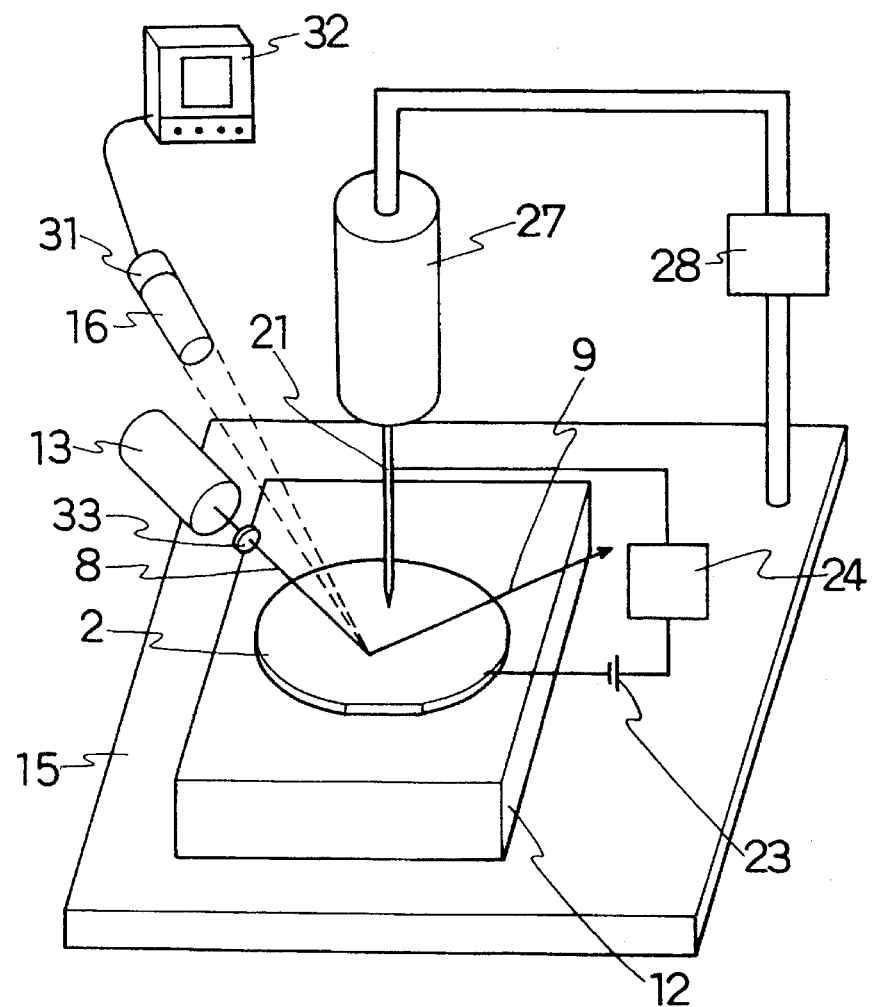
FIGS. 8(a) and 8(b) illustrate the basic configuration of a scanning tunnel microscope for explaining another example of the method for examining a slightly irregular surface state according to the present invention.
Figure 8B:
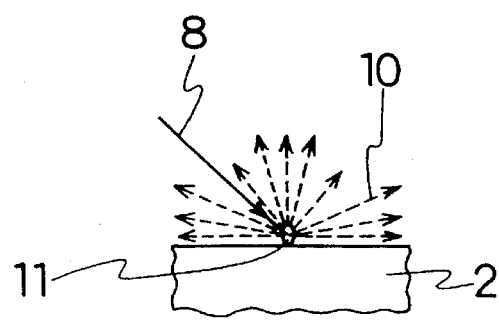

FIG. 8 illustrates the basic configuration of a scanning tunnel microscope for use in another example of the method for detecting a slightly irregular surface state according to the present invention. In FIGS. 8(a) and 8(b), a metallic probe needle 21 is connected to a second x-y actuator 15 provided for moving the probe needle 21 in x-y plane through a control system 28 of the scanning tunnel microscope, and like numerals are used to denote the same or corresponding parts of FIGS. 7(a), 7(b) and 13.

Initially, the silicon wafer 2 was set on the x-y actuator and a mirror-polished surface of the wafer 2 was illuminated with light beam 8 using the Ar laser 13, as shown in FIG. 8(a). The xyz stirring actuator 27 was then driven to lower the probe needle 21 near a surface of the wafer 2 while the second x-y actuator 15 was moved in the x-y plane, so that the light beam 8 would be applied onto a region adjacent the tip of the probe needle 21. The positional relation between the light beam 8 and the probe needle 21 was adjusted by observing the irregularly reflected light from the dark field by means of, for example, the CRT 32 connected to the microscope 16 or a photodiode, thereby centering the location of the tip of the probe needle 21 in the visual field of the microscope. Note that the location of the tip of the probe needle 21 need not necessarily be centered in the visual field and it may be placed at a predetermined location in the visual field. The objective lens and eyepiece of the microscope used this time each had X5 magnification, and the microscope was able to cover a visual field of about 2 mm diameter at the largest. The coordinates indicated by the second x-y actuator 15 at this moment were ($x_3,y_3$). The focusing point of the microscope 16 was made to coincide with the location on the silicon wafer 2 where the light beam 8 was reflected. Where a photodiode or the like is used instead of the microscope, the photodiode should be disposed as facing opposite to such location where the light beam 8 is reflected.

In turn, the xyz stirring actuator 27 was driven to make the probe needle 21 go away from the surface of the wafer 2.

The silicon wafer 2 was then moved to a position coincident with the location where the slightly irregular surface state 11 was considered to be present, i.e., the location of which approximate coordinates had been previously detected using the particle detector, by moving the second x-y actuator 15 so as to bring the wafer to the target position where the light beam should be applied.

In turn, the surface of the silicon wafer 2 was observed from the dark field section by moving the x-y actuator in the x-y plane. When the slightly irregular surface state was present on the surface, irregularly reflected light 10 was observed at the coordinates ($x_4,y_4$) defined by the x-y actuator 12 (refer to FIG. 8(b)). With respect to the silicon wafers 2 thus evaluated, reflected light was assuredly observed at least one point within the visual field of about 2 mm diameter covered by the microscope, such point being coincident with the approximate coordinates of the location where the slightly irregular surface state 11 was considered to be present on the surface of the silicon wafer 2 which had been previously detected by the particle detector. Note that the evaluation was facilitated and the best contrast ratio was obtained when the light beam was s-polarized light obtained by adjusting the polarizer 33 relative to the surface of the silcon wafer 2. Assuming that location nn where reflected light was observed is the location of slightly irregular surface state n, the location nn was centered in the visual field of the microscope, and the coordinates ($X_{nn},y_{mm}$) indicated by the x-y actuator 12 were registered as the location of the slightly irregular surface state n.

Then, the x-y actuator 12 or the second x-y actuator 15 was moved a distance ($x_{nn}-x_3,y_{mm}-y_3$) and then the xyz stirring actuator 7 was adjusted to bring the probe needle 21 into contact with the surface of the silicon wafer 2. In this way the measurement using the scanning tunnel microscope was performed.

Thus, the three-dimensional shape of the slightly irregular surface state n observed at ($x_{nn},y_{mm}$) was measured, and the results of the measurement were similar to those of Example 5.

EXAMPLE 7

Figure 9A:
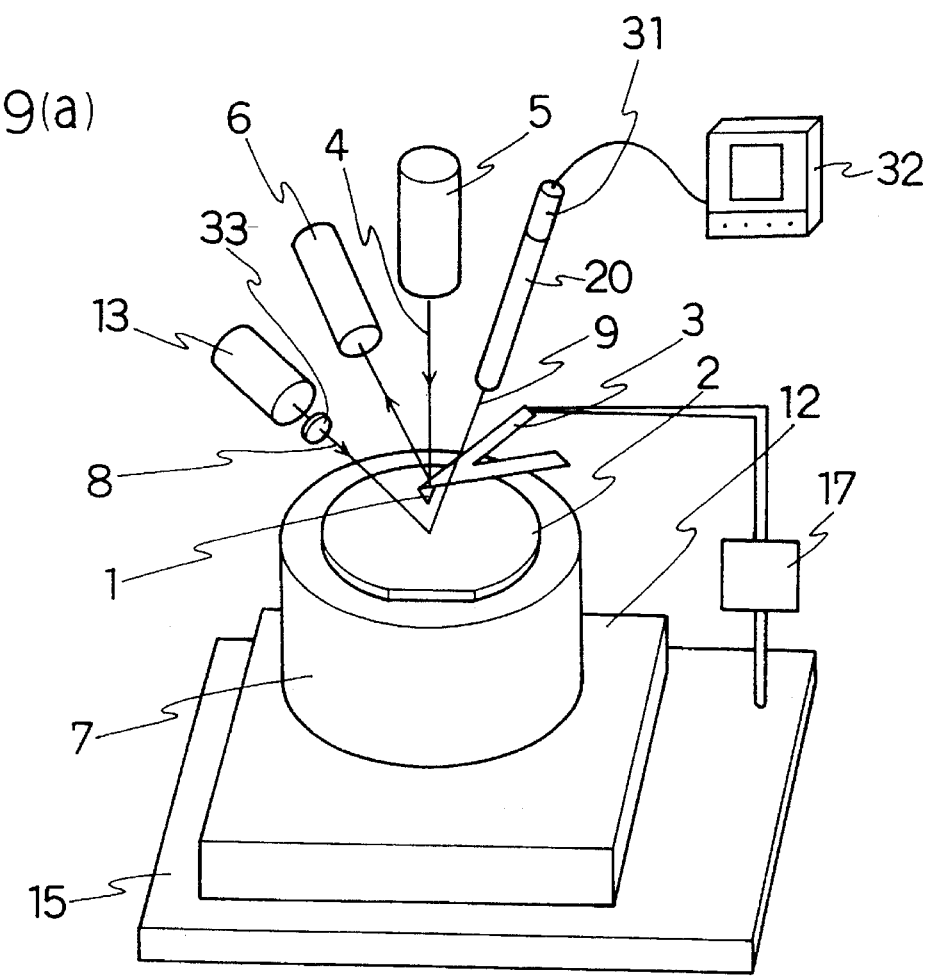
FIGS. 9(a) and 9(b) illustrate yet another example of the method for examining a slightly irregular surface state with the use of an atomic force microscope according to the present invention.
Figure 9B:
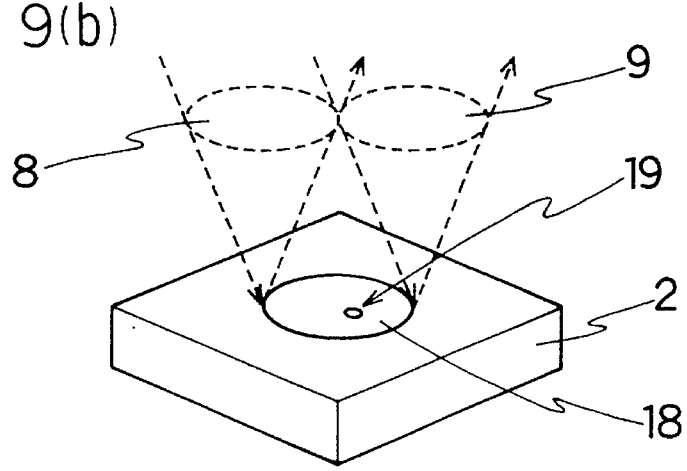

FIGS. 9(a) and 9(b) illustrate the basic configuration of an atomic force microscope as an example of the scanning probe microscope for use in one example of the method for detecting a slightly irregular surface state according to the present invention. In FIGS. 9(a) and 9(b), a CCD camera 31 having an image intensifier is mounted on a microscope 20, and a CRT 32 is adapted to output the image of the sample at observed position. In FIGS. 9(a) and 9(b), same numerals are used to denote same or corresponding parts of FIGS. 7(a), 7(b), 12(a) and 12(b).

Initially, in the same manner as in Examples 5 and 6, silicon wafer 2 was set on the xyz stirring actuator 7 as shown in FIG. 9(a), and the positional relation between the Ar laser 13 and the probe needle 1 was adjusted to center the location of the tip of the probe needle 1 in the visual field of the microscope. The coordinates indicated by the second x-y actuator 15 at this moment were considered to be $(x_0,y_0)$. The focusing point of the microscope 20 was made to coincide with the location on the silicon wafer 2 where the light beam 8 was reflected. Where a photodiode or the like is used instead of the microscope, the photodiode should be disposed so as face opposite to such location where the light beam 8 is reflected.

In turn, the xyz stirring actuator 7 was driven to make the probe needle 1 go away from the surface of the wafer 2.

The silicon wafer 2 was then moved to a position coincident with the location where the slightly irregular surface state 11 was considered to be present, i.e., the location of which approximate coordinates had been previously detected using the particle detector, by moving the second x-y actuator 15 so as to bring the wafer 2 to the target position where the light beam should be applied.

In turn, the surface of the silicon wafer 2 was observed using the microscope 20 disposed in the bright field by moving the x-y actuator 12 in the x-y plane. When the slightly irregular surface state 11 was present within the beam spot 18 of the light beam 8 applied onto the surface of the silicon wafer 2 from the Ar laser 13, the slightly irregular surface state 11 interfered with regular reflection of the light beam 8 running toward the slightly irregular surface state 11. This caused a dark portion 19 to appear at the location of the slightly irregular surface state 11 when the reflected light 9 was observed from the bright field section (refer to FIG. 9(b)). Thus, the coordinates $(x_1,y_1)$ of the location where the dark portion 19 was observed were determined.

Then, in the same manner as in Example 5, the x-y actuator 12 or the second x-y actuator 15 was moved a distance $(x_1-x_0, y_1-y_0)$ to adjust the positional relation between the probe needle 1 and the slightly irregular surface state 11. This allowed the atomic force microscope to measure the three-dimensional shape of the slightly irregular surface state 11. When the slightly irregular surface state 11 was absent within the beam spot 11, the light beam 8 was regularly reflected by the surface of the silicon wafer 2 and, hence, the reflected light 9 was not observed from the bright field section. As can be understood from the above that even if the light beam 8 is used having a spot size far larger than the slightly irregular surface state 11, the dark portion 19 attributable to the slightly irregular surface state 11 can be observed by means of the microscope 20 disposed in the bright section. Hence, the location of the slightly irregular surface state 11 within the beam spot can readily be specified with a high precision.

With respect to the silicon wafers 2 thus evaluated, at least one dark portion 19 was assuredly observed within the visual field of about 2 mm diameter covered by the microscope, the location of such a dark portion being coincident with the approximate coordinates of the location where the slightly irregular surface state 11 was considered to be present on the surface of the silicon wafer 2 which had been previously detected by the particle detector. Note that in almost all the observations only one dark portion was observed, and the observation of a plurality of dark portions was rare. Further, the contrast of the dark portion caused by a slightly irregular surface state of the order of 0.2 to 0.3 μm against the rest was higher than the contrast of the dark portion caused by a slightly irregular surface state of the order of 0.1 to 0.2 μm.

The best S/N ratio was obtained when the light beam was s-polarized light obtained by adjusting the polarizer 33 relative to the surface of the silcon wafer 2. Then, the location nm where the dark portion was observed was considered to be the location of slightly irregular surface state n, the location nm was centered or placed on a predetermined point in the visual field of the microscope, and the coordinates $(x_n,y_m)$ indicated by the x-y actuator 1Z were registered as the location of the slightly irregular surface state n.

Then, the x-y actuator 1Z or the second x-y actuator was moved a distance $(x_n-x_0, y_m-y_0)$ so that the slightly irregular surface state n would be moved to the location of the tip of the probe needle 1. The xyz stirring actuator 7 was then adjusted to bring the probe needle 1 into contact with the surface of the silicon wafer 2 so that an atomic force (repulsive force) of $10^{-9}$ would be exerted therebetween. In this way the measurement using the atomic force microscope was performed.

Thus, the three-dimensional shape of the slightly irregular surface state n observed at $(x_n,y_m)$ was measured using the atomic force microscope as in Example 5.

EXAMPLE 8

FIGS. 10(a) and 10(b) illustrate the basic configuration of a scanning tunnel microscope for use in another example of the method for detecting a slightly irregular surface state according to the present invention. In FIGS. 8(a) and 8(b), numeral 20 denotes a microscope provided for observing from a bright field section a surface of the silicon wafer 20 illuminated by Ar laser 13. A CCD camera 31 having an image intensifier is mounted on the microscope 20, and a CRT 32 is adapted to output the image of the sample at observed position. A metallic probe needle 21 is connected to a second x-y actuator 15 through the control system of the scanning tunnel microscope. In FIGS. 10(a) and 10(b) like numerals are used to denote the same or corresponding parts of FIGS. 8(a) and 8(b) and 13.

Initially, in the same manner as in Example 5, a plurality of mirror-polished silicon wafers 2 were subjected to a particle detector to observe the approximate size or location of a slightly irregular surface state present on the silicon wafers 2.

In turn, in the same manner as in Example 6, each silicon wafer 2 was set on the x-y actuator 12 and a surface of the silicon wafer 2 was then illuminated with the light beam 8 using the Ar laser 13, as shown in FIG. 10(a). The xyz stirring actuator 27 was then driven to lower the probe needle 21 near a surface of the wafer 2, and the second x-y actuator 15 was moved in the x-y plane so that the light beam 8 would be approximately applied onto a region adjacent the tip of the probe needle 21. The positional relation between the beam spot of the light beam 8 and the probe needle 21 was adjusted so as to approximately illuminate a region adjacent the tip of the probe needle 21 by observing the beam spot by means of, for example, the CRT 32 connected to the microscope 20 or a photodiode, thereby centering the location of the tip of the probe needle 21 in the visual field of the microscope 20. Note that the location of the tip of the probe needle 21 need not necessarily be centered in the visual field, and it may be placed on a predetermined point in the visual field. The objective lens and eyepiece of the microscope used here had X5 magnification and X20 magnification, respectively, and the microscope was able to cover a visual field of about 2 mm diameter at the largest setting. The coordinates indicated by the second x-y actuator 15 at this moment were $(x_3, y_3)$. The focusing point of the microscope 20 was made to coincide with the location on the silicon wafer 2 where the light beam 8 was reflected. Where a photodiode or the like is used instead of the microscope, the photodiode should be disposed so as to face opposite to such location where the light beam 8 is reflected.

The xyz stirring actuator 27 was then driven to cause the metallic probe needle 21 to move away from the surface of the silicon wafer 2.

In turn, the silicon wafer 2 was moved to a position coincident with the location where the slightly irregular surface state 11 was considered to be present, i.e., the location of which approximate coordinates had been previously detected using the particle detector, by moving the second x-y actuator 15 so as to bring the wafer 2 to the target position where the light beam 8 should be applied.

In turn, the surface of the silicon wafer 2 was observed from the bright field section by moving the x-y actuator 12 in the x-y plane, as in the foregoing examples. When the slightly irregular surface state 11 was present within the beam spot 18, a dark portion 19 was observed at the coordinates $(x_4, y_4)$ defined by the x-y actuator 12 (refer to FIG. 10(b)).

With respect to the silicon wafers 2 thus evaluated, at least one dark portion 19 was assuredly observed within a visual field of about 2 mm diameter covered by the microscope, the location of such a dark portion being coincident with the approximate coordinates of the location where the slightly irregular surface state was considered to be present on the surface of the silicon wafer 2 which had been previously detected by the particle detector. The best contrast ratio was obtained and the evaluation was facilitated when the light beam was s-polarized light obtained by adjusting the polarizer 33 relative to the surface of the silicon wafer 2. Assuming that location nn where the dark portion 19 was observed is the location of slightly irregular surface state n, the location nn was centered in the visual field of the microscope, and the coodinates $(x_{nn}, y_{mm})$ indicated by the x-y actuator 12 at this moment were registered as the location of the slightly irregular surface state n.

Then, the x-y actuator 12 or the second x-y actuator 15 was moved a distance $(x_{nn}-x_0, y_{mm}-x_3)$, and thereafter the xyz stirring actuator 27 was adjusted to bring the probe needle 21 into contact with the surface of the silicon wafer 2. In this way, the measurement was performed using the scanning tunnel microscope.

The three-dimensional measurement thus carried out on the slightly irregular surface state n observed at $(X_{nn}, y_{mm})$ gave the same result as in Example 5.

EXAMPLE 9

This example is an example of a method for fabricating a semiconductor device according to the present invention where the atomic force microscope according to the present invention was used to examine a slightly irregular surface state on a surface of a semiconductor wafer in a semiconductor device production process.

For example, to form aluminum interconnection on an insulating film covering a silicon wafer, an aluminum film was formed to a thickness of about 0.05 to about 0.5 µm on the entire surface by sputtering or a like process. Thereafter, the location of a slightly irregular surface state present on a surface of the wafer was approximately specified and the coordinates (x,y) of the approximate location were examined using a conventional particle detector.

In turn, the silicon wafer was placed on the x-y stage of the atomic force microscope and positioned by utilizing the center of the wafer which was defined based on the orientation flat of the wafer and three points on the circumference thereof.

The allowable error of the coordinates (x,y) between the particle detector and the atomic force microscope ranged from about ±100 to about ±500 µm. A light beam of the atomic force microscope was applied onto a region adjacent the coordinates (x,y), or the location of the slightly irregular surface state detected by the particle detector, thereby exactly specifying the location of the slightly irregular surface state and measuring the shape thereof in the manner described in the foregoing examples. Although there existed an error of about ±100 to about ±500 µm with respect to the coordinates (x,y) between the particle detector and the atomic force microscope as described above, positional deviation due to such an error was within the range covered by a light beam having a spot size of about 2000 to about 5000 µm. Thus, the location of the slightly irregular surface state was exactly specified with ease.

The conventional particle detector is capable of detecting only a relatively large slightly irregular surface state and, hence, inspection by the particle detector does not allow one to judge whether or not the slightly irregular surface state deleteriously affects the semiconductor device. The present invention, in contrast, is able to exactly specify the location of a slightly irregular surface state and allows one to three-dimensionally appreciate the shape of the slightly irregular surface state immediately, for example, projection or pit, or the depth and width of a recessed slightly irregular surface state. Where the patterning for interconnection follows the inspection, a fine or micro pit present on the surface, not a fine or micro projection on the surface in this case, can be a cause of a break in the interconnection since an aluminum interconnection film may be absent or made too thin or too narrow in the fine pit present on the surface. Hence, such a slightly irregular surface state can be a defect depending on the depth or width thereof. According to the design rule of submicron order, in interconnection lines having a width of 0.5 µm or smaller the presence of a narrow portion which is smaller in width by ⅕ than the normal portion is considered to degrade the reliability of the device. Stated otherwise, the presence of a pit on the surface having a depth larger by ⅕ than the thickness of an interconnection line having a width of 0.1 µm or larger. Accordingly, if a wafer has such fine pits amounting 5% of all the slightly irregular surface states detected by the particle detector, the result of the inspection may be fed back to the aluminum interconnection formation step to inform that defects such as dust or peeled portion of film caused by released dust are present on the wafer, thereby improving the production yield. In addition, since the location of each slightly irregular surface state is exactly specified, there can be specified a chip having a slightly irregular surface state that will cause a failure.

Although in this example the inspection process was carried out after the aluminum interconnection film formation step, sampling inspection or 100% inspection according to the present invention may be carried out at a certain step or each step of various semiconductor device fabrication steps that are repeatedly performed such as cleaning, ion diffusion, film formation, exposure and etching.

Further, although this example used the atomic force microscope, the use of another scanning probe microscope such as the scanning tunnel microscope will permit similar inspection.

According to the present example, the location of each slightly irregular surface on a semiconductor wafer can be exactly specified in a semiconductor device production process. The results of the inspection can be fed back to each step of the production process, while defective products can be eliminated. This will contribute to improved production yield in the production process and to products of improved reliability.

Further, according to the present example, a slightly irregular surface state smaller than 0.1 µm that cannot be detected by the conventional particle detector can be found out. In addition, it is possible to examine a slightly irregular surface state that is smaller than and lies adjacent a slightly irregular surface state detected by the particle detector. Hence, the method according to the present example can assist in clearing up the cause of a slightly irregular surface state detectable by the particle detector.

EXAMPLE 10

This example is an example of a method for fabricating a liquid crystal display device according to the present invention wherein a slightly irregular surface state on a transparent insulative substrate was analyzed by using the atomic force microscope in a liquid crystal display device production process.

In general, a liquid crystal display device is fabricated in the following manner. Initially, a TFT substrate is formed by providing on a transparent insulative substrate such as a glass substrate a thin film transistor (hereinafter referred to as "TFT") as a switching element for each pixel, gate interconnection and source interconnection between pixels, a pixel electrode for each pixel and the like. In turn, a counterpart substrate is formed by providing an electrode on a substrate. In turn, these substrates are disposed in opposing relation with each other with a predetermined gap defined therebetween and then bonded to each other at their marginal portion. Finally, a liquid crystal material is introduced into the gap between the two substrates. With increasing demand for highly miniaturized components of a liquid crystal display device and for increased rate of hole area permitting light to pass therethrough, the signal interconnection lines such as gate interconnection have been narrowed, and the space between adjacent pixels has also been narrowed. As a result, a break of a signal interconnection line and a short-circuit between such interconnection lines are likely to occur.

The process for forming the TFT substrate includes various steps such as film formation, exposure and etching. In this example the aforementioned atomic force microscope according to the present invention was used after the metal film formation step for forming gate electrodes and gate interconnection to examine and analyze a slightly irregular surface state present on a surface of a transparent insulative substrate entirely covered with a metal film such as tungsten film having a thickness of about 0.1 to about 1 µm.

As with the case of a semiconductor wafer, a particle detector was used to approximately specify the location of the slightly irregular surface state on a film surface. In turn, the transparent insulative substrate was placed on the x-y stage of the atomic force microscope and positioned by making a marked portion coincide with the reference point of the stage.

The allowable error of the coordinates (x,y) between the particle detector and the atomic force microscope ranged from about ±100 to ±500 µm. As in Example 9, the location of the slightly irregular surface state was exactly specified by the positioning method of the present invention.

Thereafter, the slightly irregular surface state was observed using the atomic force microscope and as a result the three-dimensional shape thereof was appreciated. If the slightly irregular surface state is judged to cause a failure on the basis of the shape thereof, fine projection or pit, or the size or depth thereof, the results of the inspection may be fed back to the metal film formation step, thereby reducing the number of occurrences of failures caused by such a slightly irregular surface state.

Although in this example the aluminum film for interconnection was analyzed, sampling inspection or 100% inspection according to the present invention may be carried out after any fabrication step such as insulative film formation step or etching step.

Further, although this example used the atomic force microscope, the scanning tunnel microscope may be used instead.

According to the present example, the location of each slightly irregular surface state on a transparent insulative substrate can be exactly specified in a liquid crystal display device production process. The results of the inspection can be fed back to each step of the production process to eliminate defective products. This will contribute to improved production yield of a liquid crystal display device having highly miniaturized multiple pixel and to a device of improved reliablity.

It should be appreciated that although each of the foregoing examples used an Ar laser as the light source for emitting light beam for detecting a slightly irregular surface state, the light source is not limited to the Ar laser and may be another laser light source such as a semiconductor laser or any other light source that emits light beam obtained by reducing infrared ray, white light, visible light, ultraviolet ray or the like into a beam. The positional relation between the sample 2 and the probe needle of the microscope was adjusted by moving the sample 2 (silicon wafer) by means of the x-y actuator 12. Such positional relation may be achieved by moving the probe needle by means of the second x-y actuator. Further, in each of the foregoing examples, the second x-y actuator was provided so as to initially locate the probe needle. However, the second x-y actuator is not necessarily needed if the probe needle is kept stationary and the location thereof is specified. Features other than described of the atomic force microscope or scanning tunnel microscope of the present invention are similar to those of the conventional atomic force microscope or scanning tunnel microscope, and the configuration of the microscope of the invention may be modified as far as the functions thereof are exhibited.

Further, it should be appreciated that although Examples 5 to 8 used a silicon wafer as the sample 2, the sample 2 is not limited to a silicon wafer and may be another flat substrate ( including a substrate having a slightly uneven surface) such as a transparent insulative substrate.

As has been described, according to the present invention a surface of a sample is illuminated with light beam for detecting a slightly irregular surface state present on the surface, and irregularly reflected light or a dark portion of the beam spot is observed from the dark or bright field section by means of a light beam variation sensor such as a microscope or a photodiode to specify the location of the slightly irregular surface state. Further, the probe needle of the scanning probe microscope or the slightly irregular surface state is moved relative to each other. This allows the probe needle to contact only the region of the sample where the slightly irregular surface state is present. Furthermore, when a particle detector is used in combination with an analyzer in the present invention and even if a deviation of several thousand microscopes occurs between the coordinate system of the particle detector and that of the analyzer when these coordinate system are linked to each other, a slightly irregular surface state can be detected and the location thereof can be specified in terms of the coordinate system of the analyzer by observing the variation of light beam having a beam spot size covering such a deviation.

The likelihood of an oversight can be reduced since the scanning probe microscope of the present invention analyzer is possible to detect a slightly irregular surface state that is undetectable by the particle detector.

Accordingly, a slightly irregular surface state present in the immense surface of the sample can easily be detected, while at the same time three-dimensional measurement can be performed on a selected and limited region of the sample where the slightly irregular surface state is present. This allows the time period of the measurement to be substantially reduced thereby promptly evaluating the quality of the sample.

Further, the method for fabricating a semiconductor device or a liquid crystal display device according to the present invention is capable of detecting and examining slightly irregular surface states present on a semiconductor wafer or a transparent insulative substrate and appropriately coping with these slightly irregular surface states. This contributes to a reduction in the number of occurrences of defects even in a microscopic pattern of submicron order or smaller order and to an improvement in the production yield of even a VLSI having a very high integration density. In addition, a defect which may cause a failure during use of the semiconductor device can be eliminated, thus resulting in a device of substantially improved reliability.

While only certain presently preferred embodiments have been described in detail, as will be apparent with those familiar with the art, certain changes and modifications can be made without departing from the spirit and scope of the invention as defined in the following claims.

What is claimed is:

1. A method for detecting a slightly irregular surface state, comprising the steps of:

illuminating a surface of a sample with a light beam for detecting the slightly irregular surface state;

observing a local variation of the light beam occurring due to the slightly irregular surface state within a beam spot of said light beam, and identifying a position of said local variation to specify the location of the slightly irregular surface state in an x-y plane of the sample.

2. The method of claim 1, wherein said light beam is a laser light beam.

3. The method of claim 1, wherein said variation of said light beam is observed by sensing irregularly reflected light of said light beam from a dark field section of said light beam.

4. The method of claim 3, wherein said variation of said light beam is observed by means of a light-receiving element disposed as facing opposite to the beam spot of said light beam on the surface of said sample.

5. The method of claim 1, wherein said variation of said light beam is observed by sensing a dark portion of said light beam from a bright field section of said light beam.

6. The method of claim 1, wherein said variation of said light beam is observed by focusing a microscope on the beam spot of said light beam on the surface of said sample.

7. A method for examining a slightly irregular surface state, comprising the steps of:

illuminating a surface of a sample with a light beam for detecting the slightly irregular surface state;

observing a variation of the light beam occurring due to the slightly irregular surface state to specify the location of the slightly irregular surface state in an x-y plane of the sample;

making the location of a probe needle of a scanning probe microscope and the location of the slightly irregular surface state on the sample coincide with each other; and measuring a three-dimensional image of the slightly irregular surface state by means of the scanning probe microscope.

8. The method of claim 7, wherein said step of making the location of said probe needle of a scanning probe microscope and the location of the slightly irregular surface state on the sample coincide with each other includes the steps of:

bringing said probe needle of said scanning probe microscope near the sample;

observing a variation of said light beam occurring due to said probe needle to set the location of said probe needle in said x-y plane as coordinates $(x_0, y_0)$;

finding coordinates $(x_1, y_1)$ of the location of said slightly irregular surface state on said sample specified in said x-y plane; and moving said probe needle or said sample a distance $(x_1-x_0, y_1-y_0)$.

9. The method of claim 7, wherein said sample is a semiconductor device under fabrication or a semiconductor wafer on which the semiconductor device is being fabricated in a production process.

10. The method of claim 7, wherein said sample is a liquid crystal display device under fabrication or a transparent insulative substrate on which the liquid crystal display device is being fabricated in a production process.

11. A method for fabricating a semiconductor device comprising the steps of: cleaning, ion implantation, ion diffusion, CVD, etching, exposure and heat treatment, wherein at least one of the steps includes an inspection step utilizing a method as recited in claim 7.

12. A method for fabricating a liquid crystal display device, comprising the steps of:

forming a TFT substrate having at least a thin film transistor and a pixel electrode on a transparent insulative substrate;

forming a counterpart substrate having an opposing electrode;

disposing the TFT substrate and the counterpart substrate in opposing relation with each other with a predetermined gap defined therebetween and bonding these substrates at a marginal portion thereof; and introducing a liquid crystal material into the gap, wherein the step of forming the TFT substrate or the counterpart substrate includes the steps of: cleaning, film formation, exposure, etching and ion implantation, CVD and heat treatment at least one of these steps involving an inspection step for examing a slightly irregular surface state as recited in claim 7.

13. A scanning probe microscope for measuring a three-dimensional image of a surface of a sample, comprising:

an xyz actuator for three-dimensionally adjusting a position of a probe needle of the scanning probe microscope or the sample to bring the probe needle near the sample;

a light source for providing a light beam for detecting a slightly irregular surface state present on the surface of the sample;

a light beam variation sensor, disposed in a dark field section of the light beam, for sensing irregularly reflected light of the light beam caused by the slightly irregular surface state; and an x-y actuator for specifying the location of the slightly irregular surface state.

14. The scanning probe microscope of claim 13, wherein said light source is a laser light source.

15. A method for fabricating a semiconductor device comprising the steps of: cleaning, ion implantation, ion diffusion, CVD, etching, exposure and heat treatment, wherein at least one of the steps includes an inspection step utilizing a scanning probe microscope as recited in claim 13.

16. A method for fabricating a liquid crystal display device, comprising the steps of:

forming a TFT substrate having at least a thin film transistor and a pixel electrode on a transparent insulative substrate;

forming a counterpart substrate having an opposing electrode;

disposing the TFT substrate and the counterpart substrate in opposing relation with each other with a predetermined gap defined therebetween and bonding these substrates at a marginal portion thereof; and introducing a liquid crystal material into the gap, wherein the step of forming the TFT substrate or the counterpart substrate includes the steps of: cleaning, film formation, exposure, etching, ion implantation, CVD and heat treatment at least one of these steps involving an inspection step for examining a slightly irregular surface state by means of a scanning probe microscope as recited in claim 13.

17. A scanning probe microscope for measuring a three-dimensional image of a surface of a sample, comprising:

an xyz actuator for three-dimensionally adjusting a position of a probe needle of the scanning probe microscope or the sample to bring the probe needle near the sample;

a light source for providing a light beam for detecting a slightly irregular surface state present on the surface of the sample;

a light beam variation sensor, disposed in a bright field section of the light beam, for sensing a dark portion of the light beam developed by the slightly irregular surface state; and an x-y actuator for specifying the location of the slightly irregular surface state.

18. An atomic force microscope for measuring a three-dimensional image of a surface of a sample, comprising:

a cantilever;

a probe needle mounted on a tip of the cantilever and which can be brought near the surface of the sample;

a light-emitting element and a light-receiving element which are provided for detecting a bending degree of the cantilever;

an xyz actuator for three-dimensionally adjusting a position of the sample or the cantilever;

a light source for providing a light beam for detecting a slightly irregular surface state present on the surface of the sample; and an x-y actuator capable of specifying the location of the slightly irregular surface state present on the surface of the sample.

19. A scanning tunnel microscope for measuring a three-dimensional image of a surface of a sample, comprising:

a metallic probe needle which can be brought near the surface of the sample for making tunnel current flow between the sample and the metallic probe needle;

an xyz actuator for three-dimensionally adjusting a position of the metallic probe needle or the sample;

a light source for providing a light beam for detecting a slightly irregular surface state present on the surface of the sample; and an x-y actuator capable of specifying the location of the slightly irregular surface state present on the surface of the sample.

20. A method for detecting a slightly irregular surface state, comprising the steps of:

specifying the location of the slightly irregular surface state present on a surface of a sample by means of a particle detector;

transferring the sample onto a coordinate stage of a scanning probe microscope;

approximately linking the location of the slightly irregular surface state specified by the particle detector to a coordinate system of the coordinate stage of the scanning probe microscope;

illuminating with a light beam a limited region of the surface of the sample which includes the location of the slightly irregular surface state represented in terms of the coordinate system of the coordinate stage to again specify the location of the slightly irregular surface state; and registering the location of the slightly irregular surface state again specified in terms of the coordinate system of the scanning probe microscope.

21. The method of claim 20, wherein said limited region covers all regional ranges of errors which are possible to occur when positional information of the slightly irregular surface state obtained by said particle detector is transmitted to said scanning probe microscope.

22. The method of claim 20, wherein said light beam is a laser light beam.

23. The method of claim 20, wherein said light beam is s-polarized light.

24. The method of claim 20, wherein the second detection of the slightly irregular surface state is achieved by detecting irregularly reflected light of said light beam from a dark field section of the light beam.

25. The method of claim 20, wherein the second detection of the slightly irregular surface state is achieved by detecting a dark portion developed by irregularly reflected light of said light beam from a bright field section of the light beam.

26. The method of claim 20, wherein the second detection of the slightly irregular surface state is achieved by observing the slightly irregular surface state through a microscope focusing onto the beam spot of said light beam on the surface of the sample.

27. The method of claim 26, wherein said microscope is provided with a CCD camera at an eyepiece portion thereof.

28. The method of claim 27, wherein said CCD camera has an image intensifier.

29. The method of claim 26, wherein said microscope has a visual field which is larger than the region covering the regional ranges of errors.

30. The method of claim 20, wherein the second detection of the slightly irregular surface state is achieved using a light-receiving element.

31. The method of claim 30, wherein said light-receiving element is capable of sensing reflected light from a region of the surface of the sample which is larger than the region covering the regional ranges of errors.

32. The method of claim 20, wherein said scanning probe microscope is an atomic force microscope as recited in claim 14.

33. The method of claim 20, wherein said scanning probe microscope is a scanning tunnel microscope as recited in claim 15.

34. The method of claim 20, wherein said sample is a semiconductor device under fabrication or a semiconductor wafer on which the semiconductor device is being fabricated in a production process.

35. The method of claim 20, wherein said sample is a liquid crystal display device under fabrication or a transparent insulative substrate on which the liquid crystal display device is being fabricated in a production process.

36. A method for fabricating a semiconductor device comprising the steps of: cleaning, ion implantation, ion diffusion, CVD, etching, exposure and heat treatment, wherein at least one of the steps includes an inspection step utilizing a method for detecting a slightly irregular surface state as recited in claim 20.

37. A method for fabricating a liquid crystal display device, comprising the steps of:

forming a TFT substrate having at least a thin film transistor and a pixel electrode on a transparent insulative substrate;

forming a counterpart substrate having an opposing electrode;

disposing the TFT substrate and the counterpart substrate in opposing relation with each other with a predetermined gap defined therebetween and bonding these substrates at a marginal portion thereof; and introducing a liquid crystal material into the gap, wherein the step of forming the TFT substrate or the counterpart substrate includes the steps of: cleaning, film formation, exposure, etching and ion implantation, at least one of these steps involving an inspection step for detecting a slightly irregular surface state by a method as recited in claim 20.

* * * * *